United States Patent [19]

Sanchez

[11] Patent Number: 5,420,173
[45] Date of Patent: May 30, 1995

[54] MULTI-COMPONENT ETHYLENICALLY UNSATURATE PEROXYESTERS

[76] Inventor: Jose Sanchez, 1624 Huth Rd., Grand Island, N.Y. 14072

[21] Appl. No.: 220,148

[22] Filed: Mar. 30, 1994

[51] Int. Cl.$^6$ .............................................. C08F 2/46
[52] U.S. Cl. ..................... 522/104; 528/272;
528/274; 528/306; 525/437; 525/444; 526/203;
526/228; 526/230; 526/323; 526/335; 522/24;
522/28; 522/60; 522/63; 522/65; 522/67;
522/68; 522/71; 522/93; 522/102
[58] Field of Search ............ 528/272, 274, 306;
525/437, 444; 526/203, 228, 230, 323, 335;
522/24, 28, 60, 63, 65, 67, 68, 71, 93, 102, 104

[56] References Cited

U.S. PATENT DOCUMENTS 3,536,676  10/1970  Mageli et al. .......................... 525/61
3,763,112  10/1973  Bafford et al. ......................... 526/201

FOREIGN PATENT DOCUMENTS 1041088  9/1966  United Kingdom .

OTHER PUBLICATIONS

Visn, L'viv. Politekh, Inst., 1974, 82,24–7 (Translation and Original).
Chem. Abs., 105, (20): 17323Ls (1986)–Abstracting Japanese Patent Appln. 84/209679.

Primary Examiner—Samuel A. Acquah

[57] ABSTRACT

A novel and safe ethylenically unsaturated peroxyester composition derived from an ethylenically unsaturated dicarboxylic acid is provided, as well as processes for making and using the composition. The peroxyester composition comprises about 0.04 to about 0.70 mole fraction of a first component compound having a formula I:

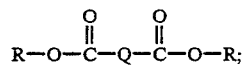

about 0.32 to about 0.50 mole fraction of a second component compound having a formula II:

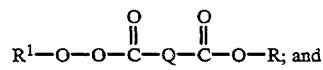

about 0.04 to about 0.70 mole fraction of a third component compound having a formula III:

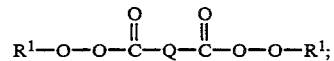

wherein Q is an unsaturated ethylene divalent radical and $R^1$ and $R^2$ are organic substituents. Polymeric-peroxides are prepared via polymerizing the peroxyester compositions. The peroxyester compositions are also used for curing unsaturated polyester resins and for initiating polymerization of ethylenically unsaturated monomers.

10 Claims, 1 Drawing Sheet

MULTI-COMPONENT ETHYLENICALLY UNSATURATE PEROXYESTERS

BACKGROUND OF THE INVENTION

1. Field of the Invention

This invention relates to novel and safe multi-component ethylenically unsaturated peroxyester compositions derived from ethylenically unsaturated dicarboxylic acids and methods of preparing them. This invention further relates to using these peroxyester compositions for curing unsaturated polyester resins and for initiating polymerization of ethylenically unsaturated monomers. The present invention also relates to using these peroxyester compositions for preparing polymeric peroxides produced therefrom. The polymeric peroxides derived from the novel and safe ethylenically unsaturated peroxyester compositions of the present invention are effective in preparing graft copolymer compositions having utility in compatibilizing polymeric blends and alloys.

2. Description of the Prior Art

A peroxymonomer, such as a di-t-alkyl diperoxyfumarate (e.g., di-t-butyl diperoxyfumarate), is a valuable composition for preparing a polymeric peroxide. A diperoxyfumarate can copolymerize with another ethylenically unsaturated monomer to form a peroxide-containing copolymer, as well as react with a polymer possessing labile carbon-hydrogen (C—H) bonds to subsequently form a peroxide-containing polymer.

Many newly commercialized polymeric materials are polymeric blends and alloys composed of two or more different polymers. This trend of commercially developing polymeric blends and alloys is attractive because of the ability to develop polymeric blends and alloys that are "tailor made" to meet end-use property specifications, among other reasons. Blending polymers may also result in polymer property improvements including:

(1) better processability;
(2) impact strength enhancement,
(3) improved flame retardance,
(4) improved barrier properties,
(5) improved tensile properties,
(6) improved adhesion,
(7) improved melt flow,
(8) enhanced heat distortion temperature (HDT),
(9) enhanced heat resistance,
(10) improved stiffness,
(11) improved chemical resistance, and
(12) improved ultraviolet light stability.

The major problem encountered in developing new polymeric blends and alloys is the inherent incompatibility or immiscibility of almost all mixtures of two or more polymers. The consequence of incompatibility of polymeric blends and alloys is that they are thermodynamically unstable and, consequently, do not have good mechanical and thermal properties. With sufficient time and temperature, the polymeric blends and alloys generally coalesce into separate phases. An approach used by resin compounders to improve the compatibility of immiscible blends is to use a block or graft copolymer as a compatibilizing agent for the incompatible polymer blend. Generally, block and graft copolymers that are effective compatibilizing agents for polymeric blends and alloys possess at least two unlike polymer segments that are individually compatible with one or the other polymeric component of the polymeric blends and alloys, thereby enabling formation of polymeric blends and alloys having enhanced phase stability.

Low cost polymeric blends and alloys are generally commercially produced from two or more addition polymers, such as polymeric blends comprising low density polyethylene (LDPE), linear low density polyethylene (LLDPE), high density polyethylene (HDPE) and polypropylene (PP). The compatibility of these low cost polymeric blends can be improved by crosslinking the polymeric blends with peroxides or by using compatibilizing block or graft copolymers, as mentioned above.

One important use of a polymeric peroxide, such as a polymer derived from a peroxyfumarate, is in preparing a graft copolymer useful for compatibilizing polymeric blends and alloys. However, there are two major problems encountered in the potential commercialization of di-t-alkyl diperoxyfumarates of the prior art. The first problem is the generally low preparative yields of the di-t-alkyl diperoxyfumarates based upon starting material, for example, fumaryl chloride. The corrected yields for preparing the di-t-butyl diperoxyfumarate and the di-t-amyl diperoxyfumarate are generally about 50–65%, which are quite low. The second problem is the generally extreme hazard of many peroxides, exemplified by the pure diperoxyfumarate derived from lower t-alkyl hydroperoxides. Commercial peroxides react differently and often violently under various hazardous conditions, such as exposure to shock, friction, heat, flame or contamination.

One recognized measure of shock sensitivity is a Trauzl Test Number, derived from a Modified Trauzl Test, as set forth in O. L. Mageli et al., *J. Chem. Ed.*, 48, p. A451 (1971). The Trauzl Number is the cup volume expansion, in milliliters (mL), which is produced when 6 grams (g) of a test specimen is detonated in a heavy lead cup by the shock of a blasting cap. The higher the Trauzl Number, the more forceful the explosion caused by the test specimen. The Trauzl Test Numbers for pure di-t-butyl diperoxyfumarate, pure di-t-amyl diperoxyfumarate and commercial, dry 98% dibenzoyl peroxide are given below:

TABLE 1

| Trauzl Tests - Diperoxyfumarates | |
|---|---|
| Peroxide Tested | Trauzl Number, mL |
| Di-t-Butyl Diperoxyfumarate | 72 |
| Di-t-Amyl Diperoxyfumarate | 49 |
| 98% Dibenzoyl Peroxide | 28 |

The information of Table 1 indicates that pure di-t-butyl diperoxyfumarate and pure di-t-amyl diperoxyfumarate are generally significantly more hazardous than 98% dibenzoyl peroxide. However, of the commercially available organic peroxides, 98% dibenzoyl peroxide has one of the highest Trauzl Numbers. Owing to its high Trauzl Number, 98% dibenzoyl peroxide is restricted to a maximum commercial package size of one pound (i.e., one pound of 98% dibenzoyl peroxide in a paper bag package) due to hazards associated with shipping and handling the 98% dibenzoyl peroxide. In the cases of di-t-butyl diperoxyfumarate and di-t-amyl diperoxyfumarate, the maximum package size would generally have to be restricted to significantly less than one pound. Restricting a peroxide package to such a small size is costly and uneconomical.

Generally, such shipping and handling hazards can be reduced by diluting the hazardous peroxide with a generally high boiling solvent, thereby reducing the relative amount of active diperoxyfumarate used in the composition. However, pure di-t-butyl diperoxyfumarate and pure di-t-amyl diperoxyfumarate are solid materials at room temperature and, at the required storage temperatures, are not readily soluble in the high boiling solvents acceptable to the polymer industry. Generally, solid separation of the pure di-t-butyl diperoxyfumarate and pure di-t-amyl diperoxyfumarate from a solution of the di-t-butyl peroxyfumarate, di-t-amyl diperoxyfumarate and the high boiling solvent occurs, which is highly undesirable.

U.S. Pat. No. 3,536,676 discloses polymerizing di-t-alkyl diperoxyfumarate with monomers such as stryrene, vinyl acetate, vinyl chloride, acrylonitrile, methyl methacrylate and butadiene, at temperatures of about −60° C. to about 80° C. This patent discloses homopolymerization of di-t-butyl diperoxyfumarate which may be carried out as a self-initiated polymerization or using a free radical generating initiator. Yields of the homopolymer are quite low. The patent also discloses copolymerization of di-t-butyl diperoxyfumarate with various ethylenically unsaturated monomors capable of being polymerized by free radical initiation. Although several different copolymerization techniques were used, in general, the yields were low even though the reaction times were long. This patent also discloses the preparation of graft and block copolymers, resin stabilization and resin curing using the disclosed copolymers.

U.S. Pat. No. 3,763,112 discloses preparing polymeric and non-polymeric di-t-alkyl diperoxyfumarate adducts by reacting di-t-alkyl diperoxyfumarate with compounds possessing labile C—H bonds, in the presence or absence of conventional free-radical generators and/or upon exposure to actinic light (visible, ultraviolet, etc.). The results of the reaction which may be simple molecular compounds or polymeric compounds having one or more pendant diperoxysuccinyl groups are of use in preparing block and graft copolymers.

Japanese Patent Application 84/209679 (*Chemical Abstracts* (hereinafter "CA") 105, (20):173232s (1986)) discloses various OO-t-alkyl O-alkyl monoperoxyfumarates and the use of these monoperoxyfumarates for preparing styrene polymers having enhanced moldability. By virtue of its lower active oxygen content, the OO-t-alkyl O-alkyl monoperoxyfumarate, even when pure, is significantly less hazardous than the comparable di-t-alkyl diperoxyfumarate. However, the pure OO-t-alkyl O-alkyl monoperoxyfumarate is generally difficult and expensive to prepare commercially from fumaric acid or fumaryl chloride. For example, V. V. Shybanov et al., *Visn. L'viv. Politekh Inst.*, 82, pp. 24–27 (1974) (CA, 82, (25):169934m (1975)) discloses the time-consuming and costly stepwise preparation of OO-t-butyl O-alkyl monoperoxyfumarates by adding an alcohol to fumaryl chloride, followed by reacting overnight; lengthy isolation of the resulting intermediate (i.e., alkyl trans-3-chlorocarbonyl-2-propenoate) and subsequent treatment of the intermediate with t-butyl hydroperoxide, followed by reacting overnight and lengthy isolation of the resulting OO-t-butyl O-alkyl monoperoxyfumarate.

Furthermore, when fumaric acid is the starting material, rather than fumaryl chloride, it is necessary to initially synthesize alkyl hydrogen fumarates. Reacting one mole of fumaric acid with one mole of alcohol will produce a mixture of products composed of a dialkyl fumarate, the desired alkyl hydrogen fumarate and unreacted fumaric acid. The unreacted fumaric acid and dialkyl fumarate must be separated from the desired alkyl hydrogen fumarate, which is generally an expensive procedure. The alkyl hydrogen fumarate is then converted to an alkyl trans-3-chlorocarbonyl-2-propenoate via reaction with an acid chlorinating agent. Finally, the alkyl trans-3-chloro-carbonyl-2-propenoate is reacted with a t-alkyl hydroperoxide in the presence of base to give the desired OO-t-alkyl O-alkyl monoperoxyfumarate.

When fumaryl chloride is the starting material, the fumaryl chloride is first reacted with an alcohol to yield an impure mixture containing the desired alkyl trans-3-chlorocarbonyl-2-propenoate. This impure mixture must be purified by a costly distillation process before conducting the next stage of the synthesis process. After purifying the impure mixture by distillation, the alkyl trans-3-chlorocarbonyl-2-propenoate intermediate is reacted with a suspension of an alkali metal salt of a t-alkyl hydroperoxide in a solvent, such as $CCl_4$, thereby producing the desired OO-t-alkyl O-alkyl monoperoxyfumarate.

Hence, existing techniques of preparing a pure OO-t-alkyl O-alkyl monoperoxyfumarate result in a costly commercial product. Such a product is therefore unlikely to be available for commercially synthesizing a polymeric peroxide which is subsequently used as a graft copolymer compatibilizing agent for polymeric blends and alloys.

British Patent 1,041,088 discloses peroxide-containing copolymer compositions derived from polymerizable ethylenically unsaturated monomers and at least one unit of an unsaturated peroxyester. The ethylenically unsaturated monomers include vinyl esters, esters of acrylic acid and methacrylic acid, vinyl chloride, acrylonitrile, butadiene, isoprene, acrylamide and vinyl ethers, for example. The unsaturated peroxyesters include t-butyl peroxymethacrylate, OO-t-butyl O-hydrogen monoperoxymaleate, OO-t-butyl O-butyl monoperoxymaleate, OO-t-butyl O-butyl monoperoxyfumarate and t-butyl peroxycinnamate, for example. Polymers produced from OO-t-alkyl O-hydrogen monoperoxyfumarates and the OO-t-alkyl O-hydrogen monoperoxymaleates are expected to react at elevated temperatures via non-radical reactions to form non-peroxidic polymers and t-alkyl hydroperoxides.

t-Butyl peroxymethacrylate is difficult to prepare and is hazardous owing to very exothermic self-polymerization/decomposition. t-Butyl peroxycinnamate does not polymerize or copolymerize very readily. As indicated, OO-t-alkyl O-alkyl monoperoxyfumarates, such as OO-t-butyl O-butyl monoperoxy-fumarate, are costly to prepare due to the necessary lengthy and multi-step processes. Therefore, polymeric peroxides produced from the OO-t-alkyl O-alkyl monoperoxyfumarates via free-radical initiated polymerizations are very expensive. The same is true for OO-t-alkyl O-alkyl monoperoxymaleates, such as OO-t-butyl O-butyl monoperoxymaleate.

The novel and safe ethylenically unsaturated peroxyester compositions of the present invention are easy to prepare in better yields than those of the prior art, using a simple and rapid, low-cost process and readily available starting reactants. Therefore, the novel polymeric peroxides derived therefrom will be low in cost.

The multi-component ethylenically unsaturated peroxy ester compositions according to the the present invention overcome the problems of the prior art and are easier to prepare.

Preparations of multi-component compositions of the present invention, such as the combination of dialkyl fumarate, OO-t-alkyl O-alkyl monoperoxyfumarate and di-t-alkyl diperoxyfumarate, via a simultaneous reaction of t-alkyl hydroperoxide and alcohol with fumaryl chloride, in the presence of base, are not reported in the literature. The novel ethylenically unsaturated peroxyester compositions of the present invention are much safer than the prior art di-t-alkyl diperoxyfumarates and are inexpensively prepared in a novel, rapid, low cost process by reacting a mixture of an alcohol and a t-alkyl hydroperoxide with a di-(halocarbonyl) derivative of an ethylenically unsaturated dicarboxylic acid, in the presence of a base. No expensive distillative isolation processes are necessary in the novel processes of the present invention in contrast to the prior art processes.

In addition, the process yields for the novel and safe ethylenically unsaturated peroxyester compositions of the present invention are significantly higher than those of comparable prior art di-t-alkyl diperoxyfumarates. As a result, the peroxyester compositions of the present invention are produced at a generally low cost.

SUMMARY OF THE INVENTION

One aspect of the invention relates to a peroxyester composition comprising about 0.04 to about 0.70 mole fraction of a first component compound having a formula I:

about 0.32 to about 0.50 mole fraction of a second component compound having a formula II:

about 0.04 to about 0.70 mole fraction of a third component compound having a formula III:

the mole fractions being determined by the respective molar quantities of the three components present in the peroxyester composition;

wherein

Q is a divalent radical having a formula IV, V or VI:

R is substituted or unsubstituted alkyl of 1 to 18 carbons optionally containing one or more —O— or —NH— hetero groups, with the proviso that multiple hetero groups must be separated from each other and the radical ends by at least one carbon atom, substituted or unsubstituted cycloalkyl of 5 to 12 carbons, substituted or unsubstituted alkenyl of 3 to 11 carbons, substituted or unsubstituted aryl of 6 to 14 carbons or substituted or unsubstituted aralkyl of 7 to 11 carbons, where the R substituents are independently one or more of lower alkyl of 1 to 4 carbons, chloro, bromo, cyano, carboxy, alkoxy of 1 to 10 carbons or aryloxy of 6 to 10 carbons;

$R^1$ is substituted or unsubstituted t-alkyl of 4 to 12 carbons, substituted or unsubstituted t-alkynyl of 5 to 9 carbons, substituted or unsubstituted t-cycloalkyl of 6 to 13 carbons or substituted or unsubstituted t-aralkyl of 9 to 13 carbons, where the $R^1$ substituents are independently one or more of lower alkyl of 1 to 4 carbons, chloro, hydroxy or t-alkylperoxy of 4 to 8 carbons; and from zero to about 250% by weight of a solvent, based upon the total weight of the three components of the peroxyester composition having formulas I, II and III.

Another aspect of the invention relates to a process for preparing the above-defined novel peroxyester composition comprising reacting in the presence of an inorganic base, and optionally one or more solvents, a di-(halocarbonyl) compound having a formula VII:

with about 0.20 to about 0.80 mole fraction of an alcohol having a formula R—OH and with about 0.80 to about 0.20 mole fraction of a hydroperoxide having a formula $R^1$—O—OH, wherein Q, R and $R^1$ are as previously broadly defined;

wherein X is chloro or bromo; and isolating the peroxyester composition or a solution thereof.

Yet another aspect of the invention relates to a polymeric peroxide comprising at least three independent recurring units in the backbone of the polymer chain or pendant to the polymer chain:

a first recurring unit having a formula VIII:

a second recurring unit having a formula IX:

and a third recurring unit having a formula X:

wherein $Q^1$ is a tetrayl radical having a formula XI, XII or XIII:

-continued $$\begin{array}{c}\text{A}\\|\\-\text{C}-\text{CH}_2-\\|\\\text{CH}_2\\|\\\text{D}\end{array} \quad \text{or} \qquad \text{XII}$$

$$\begin{array}{c}\text{D}\\|\\-\text{C}-\text{CH}_2-;\\|\\\text{CH}_2\\|\\\text{A}\end{array} \qquad \text{XIII}$$

where A represents the point of bonding of $Q^1$ to the carbonyl carbon of the $$\text{R}-\text{O}-\overset{\overset{\text{O}}{\|}}{\text{C}}-$$

group of formula VIII or $$\text{R}^1-\text{O}-\text{O}-\overset{\overset{\text{O}}{\|}}{\text{C}}-$$

group of formula IX or X;

D represents the point of bonding of $Q^1$ to the carbonyl carbon of the $$-\overset{\overset{\text{O}}{\|}}{\text{C}}-\text{O}-\text{R}$$

group of formula VIII or IX or $$-\overset{\overset{\text{O}}{\|}}{\text{C}}-\text{O}-\text{O}-\text{R}^1$$

group of formula X; and

R and $R^1$ are as previously broadly defined.

This invention also comprehends using the novel peroxyester composition for curing an unsaturated polyester resin composition by heating the resin at an effective temperature with an effective amount of the novel peroxyester composition to cure the polyester resin composition.

This invention also comprehends polymerizing an ethylenically unsaturated monomer by heating the monomer in the presence of an amount of the novel peroxyester composition and at a temperature effective to initiate polymerization of the polymer.

This invention further comprehends preparing a polymeric peroxide containing recurring units of the above-identified formulas VIII, IX and X by homopolymerizing or copolymerizing the novel peroxyester composition in the presence or absence of one or more ethylenically unsaturated monomers using the peroxyester composition and/or a conventional free radical initiator to initiate polymerization.

This invention also comprehends preparing a polymeric peroxide by reacting at least one polymer or copolymer having labile carbon-hydrogen bonds with the novel peroxyester composition using radiation, the novel peroxyester composition and/or a conventional free-radical initiator to initiate polymerization.

DETAILED DESCRIPTION OF THE PREFERRED EMBODIMENTS

As mentioned above, the present invention relates to novel and safe ethylenically unsaturated peroxyester compositions, a process for making them in higher yields than those of comparable prior art di-t-alkyl diperoxyfumarates and their use in subsequent polymerization reactions and products. The present invention is based on the formation of the three-component peroxyester composition comprising about 0.04 to about 0.70 mole fraction of a first component compound having a formula I:

$$\text{R}-\text{O}-\overset{\overset{\text{O}}{\|}}{\text{C}}-\text{Q}-\overset{\overset{\text{O}}{\|}}{\text{C}}-\text{O}-\text{R}; \qquad \text{I}$$

about 0.32 to about 0.50 mole fraction of a second component compound having a formula II:

$$\text{R}^1-\text{O}-\text{O}-\overset{\overset{\text{O}}{\|}}{\text{C}}-\text{Q}-\overset{\overset{\text{O}}{\|}}{\text{C}}-\text{O}-\text{R}; \text{ and} \qquad \text{II}$$

about 0.04 to about 0.70 mole fraction of a third component compound having a formula III:

$$\text{R}^1-\text{O}-\text{O}-\overset{\overset{\text{O}}{\|}}{\text{C}}-\text{Q}-\overset{\overset{\text{O}}{\|}}{\text{C}}-\text{O}-\text{O}-\text{R}^1; \qquad \text{III}$$

the mole fractions being determined by the respective molar quantities of the three components present in the peroxyester composition.

Q is a divalent radical having a formula IV, V or VI:

$$-\text{CH}=\text{CH}-, \qquad \text{IV}$$

$$\begin{array}{c}-\overset{\overset{\text{O}}{\|}}{\text{C}}-\text{CH}_2-\\|\\\text{CH}_2\end{array} \quad \text{or} \qquad \text{V}$$

$$\begin{array}{c}-\text{CH}_2-\overset{\overset{\text{O}}{\|}}{\text{C}}-.\\|\\\text{CH}_2\end{array} \qquad \text{VI}$$

Preferably, Q is IV.

R is substituted or unsubstituted alkyl of 1 to 18 carbons optionally containing one or more —O— or —NH— hetero groups, with the proviso that multiple hetero groups must be separated from each other and the radical ends by at least one carbon atom, substituted or unsubstituted cycloalkyl of 5 to 12 carbons, substituted or unsubstituted alkenyl of 3 to 11 carbons, substituted or unsubstituted aryl of 6 to 14 carbons or substituted or unsubstituted aralkyl of 7 to 11 carbons, where the R substituents are one or more of lower alkyl of 1 to 4 carbons, chloro, bromo, cyano, carboxy, alkoxy of 1 to 10 carbons or aryloxy of 6 to 10 carbons.

Preferably, R is alkyl of 1 to 18 carbons or cycloalkyl of 5 to 12 carbons.

More preferably, R is alkyl of 1 to 18 carbons.

$R^1$ is substituted or unsubstituted t-alkyl of 4 to 12 carbons, substituted or unsubstituted t-alkynyl of 5 to 9 carbons, substituted or unsubstituted t-cycloalkyl of 6 to 13 carbons or substituted or unsubstituted t-aralkyl of 9 to 13 carbons, where the $R^1$ substituents are independently one or more of lower alkyl of 1 to 4 carbons, chloro, hydroxy or t-alkylperoxy of 4 to 8 carbons.

Preferably, $R^1$ is t-alkyl of 4 to 12 carbons or t-cycloalkyl of 6 to 13 carbons.

More preferably, $R^1$ is t-alkyl of 4 to 12 carbons.

The peroxyester composition of the present invention may also optionally contain from zero to about 250% by weight of a solvent, based upon the total weight of the three components of the peroxyester composition having formulas I, II and III.

The first component of formula I may generally be referred to as a non-peroxide component (Component I). The second component of formula II may generally be referred as a monoperoxide component (Component II). The third component having formula III may generally be referred to as a diperoxide component (Component III).

Non-limiting examples of specific compounds corresponding to Component I of the composition of the present invention are: dimethyl fumarate, di-n-butyl fumarate, dicyclohexyl fumarate, diallyl fumarate, diisopropyl fumarate, di-n-butyl maleate and di-n-butyl itaconate, among others.

Non-limiting examples of specific compounds corresponding to Component II of the composition of the present invention are: OO-t-butyl O-methyl monoperoxyfumarate, OO-t-butyl O-n-butyl monoperoxyfumarate, OO-t-butyl O-cyclohexyl monoperoxyfumarate, OO-t-butyl O-allyl monoperoxyfumarate, OO-t-amyl O-methyl monoperoxyfumarate, OO-t-amyl O-isopropyl monoperoxyfumarate, OO-(1-ethyl-1-methylpropyl) O-methyl monoperoxyfumarate, OO-(1,1,3,3-tetramethylbutyl) O-methyl monoperoxyfumarate, OO-(1-methylcyclohexyl) O-methyl monoperoxyfumarate, OO-[1,1,4,4-tetramethyl-4-(t-butylperoxy)butyl] O-methyl monoperoxyfumarate, OO-(alpha-cumyl) O-methyl monoperoxyfumarate, OO-(1,1-dimethyl-2-propynyl) O-methyl monoperoxyfumarate, OO-t-butyl O-n-butyl monoperoxymaleate and OO-t-butyl O-n-butyl monoperoxyitaconate, among others.

Non-limiting examples of specific compounds corresponding to Component III of the composition of the present invention are: di-t-butyl diperoxyfumarate, di-t-amyl diperoxyfumarate, di-(1,1,3,3-tetramethylbutyl) diperoxyfumarate, di-(1-methylcyclohexyl)diperoxyfumarate, di-[1,1,4,4-tetramethyl-4-(t-butylperoxy)butyl] diperoxyfumarate, di-(alpha-cumyl) diperoxyfumarate, di-(dimethyl-2-propynyl) diperoxyfumarate, di-t-butyl diperoxymaleate and di-t-butyl diperoxyitaconate, among others.

Non-limiting examples of the novel and safe ethylenically unsaturated peroxyester compositions of the present invention, which exist as mixtures of Component I, Component II and Component III, include:

Mixtures of dimethyl fumarate, OO-t-butyl O-methyl monoperoxyfumarate and di-t-butyl diperoxyfumarate (Component I, Component II and Component III, respectively); mixtures of di-n-butyl fumarate, OO-t-butyl O-n-butyl monoperoxyfumarate and di-t-butyl diperoxyfumarate; mixtures of dicyclohexyl fumarate, OO-t-butyl O-cyclohexyl monoperoxyfumarate and di-t-butyl diperoxyfumarate; mixtures of diallyl fumarate, OO-t-butyl O-allyl monoperoxyfumarate and di-t-butyl diperoxyfumarate; mixtures of dimethyl fumarate, OO-t-amyl O-methyl monoperoxyfumarate and di-t-amyl diperoxyfumarate, mixtures of diisopropyl fumarate, OO-t-amyl O-isopropyl monoperoxyfumarate and di-t-amyl diperoxyfumarate; mixtures of dimethyl fumarate, OO-(1-ethyl-1-methylpropyl) O-methyl monoperoxyfumarate and di-(1-ethyl-1-methylpropyl) diperoxyfumarate; mixtures of dimethyl fumarate, OO-(1,1,3,3-tetramethylbutyl) O-methyl monoperoxyfumarate and di-(1,1,3,3-tetramethylbutyl) diperoxyfumarate; mixtures of dimethyl fumarate, OO-(1-methylcyclohexyl) O-methyl monoperoxyfumarate and di-(1-methylcyclohexyl)diperoxyfumarate; mixtures of dimethyl fumarate, OO-[1,1,4,4-tetramethyl-4-(t-butylperoxy) butyl] O-methyl monoperoxyfumarate and di-[1,1,4,4-tetramethyl-4-(t-butylperoxy)butyl] diperoxyfumarate; mixtures of dimethyl fumarate, OO-(alpha-cumyl) O-methyl monoperoxyfumarate and di-(alpha-cumyl) diperoxyfumarate; mixtures of dimethyl fumarate, OO-(1,1-dimethyl-2-propynyl) O-methyl monoperoxyfumarate and di-(1,1-dimethyl-2-propynyl) diperoxyfumarate; mixtures of di-n-butyl maleate, OO-t-butyl O-n-butyl monoperoxymaleate and di-t-butyl diperoxymaleate; and mixtures of di-n-butyl itaconate, OO-t-butyl O-n-butyl monoperoxyitaconate and di-t-butyl diperoxyitaconate, among others; as well as the above compositions having added optional solvents.

Non-limiting examples of suitable optional solvents useful in and for preparing the novel and safe ethylenically vunsaturated peroxyester compositions of this invention include pentane, hexanes, heptanes, dodecanes, odorless mineral spirits mixtures, toluene, xylenes, cumene, methylene chloride, ethyl acetate, 2-ethylhexyl acetate, isobutyl isobutyrate, aliphatic diesters such as dimethyl adipate, dimethyl succinate and dimethyl glutarate or mixtures thereof, dimethyl phthalate, dibutyl phthalate, benzyl butyl phthalate, diethyl ether, methyl t-butyl ether, 2-methoxyethyl acetate, methyl butyl ketone and methyl isoamyl ketone, among others.

Preparation of the Novel and Safe Ethylenically Unsaturated Peroxyester Compositions Several synthesis methods are available for preparing the novel and safe ethylenically unsaturated peroxyester compositions in accordance with the present invention. In general, a hydroperoxide, such as a t-alkyl hydroperoxide, and an alcohol, such as an alkanol, are reacted with a di-(halocarbonyl) derivative of an ethylenically unsaturated dicarboxylic acid, e.g., fumaryl chloride, or a solution thereof, in the presence of an inorganic base, at temperatures of about $-25°$ C. to $50°$ C.

In one procedure, hereinafter "Procedure A," water, an inorganic base, a hydroperoxide, an alcohol and optionally a solvent, are mixed and vigorously stirred. Then, a neat di-(halocarbonyl) derivative of an ethylenically unsaturated dicarboxylic acid, e.g., fumaryl chloride, or a solution thereof, is added to the vigorously stirred mixture.

In another procedure, hereinafter "Procedure B," the di-(halocarbonyl) derivative of an ethylenically unsaturated dicarboxylic acid, e.g., fumaryl chloride, the t-alkyl hydroperoxide, the alcohol and the optional solvent are initially mixed together and vigorously stirred. Then, a highly concentrated (about 30% to about 60%) aqueous solution of an inorganic base is added rapidly to the vigorously stirred mixture.

In both Procedures A and B, the reaction mixture is allowed to further react for about 5 minutes to about 4 hours at a temperature about −25° C. to about 50° C. Water may then be added and the aqueous phase is separated and discarded. Then the product peroxyester composition is isolated by methods well known in the art.

More specifically, the process for preparing the peroxyester compositions of the present invention comprises reacting in the presence of an inorganic base, and optionally one or more solvents, a di-(halocarbonyl) compound having a formula VII:

with about 0.20 to about 0.80 mole fraction of an alcohol having a formula R—OH, preferably about 0.35 to about 0.65 mole fraction of alcohol, and with about 0.80 to about 0.20 mole fraction of a t-alkyl hydroperoxide having a formula $R^1$—O—OH, preferably about 0.35 to about 0.65 mole fraction of a t-alkyl hydroperoxide, and isolating the peroxyester composition or a solution thereof.

Q, R, $R^1$ and X are as previously defined. Preferably X is chloro.

The following lists of compounds are to provide specific, non-limiting, examples of the compounds which can be used to prepare the novel peroxyester compositions of the present invention.

Non-limiting examples of suitable alcohols useful for preparing the novel and safe ethylenically unsaturated peroxyester compositions of this invention include methanol, ethanol, isopropanol, 2-butanol, 2-ethylhexanol, dodecanol, cyclopentanol, cyclohexanol, cyclododecanol, allyl alcohol, crotyl alcohol, phenol, cresols, t-butylphenols, ethylphenols, 2-chloroethanol, 2-cyanoethanol and benzyl alcohol, among others.

Non-limiting examples of suitable hydroperoxides include t-butyl hydroperoxide, t-amyl hydroperoxide, 1-ethyl-1-methylpropyl hydroperoxide, 1,1-diethylpropyl hydroperoxide, 1,1,3,3-tetramethylbutyl hydroperoxide, 1,1-dimethyldecyl hydroperoxide, chloro-t-butyl hydroperoxide, 1,1,4,4-tetramethyl-4-(t-butylperoxy)butyl hydroperoxide, 1,1,4,4-tetramethyl-4-(t-amylperoxy)butyl hydroperoxide, 1-methyl-1-hydroperoxycyclohexane, 3-methyl-3-hydroperoxy-1-butyne, 3-methyl-3-hydroperoxy-1-pentyne, 1-ethynyl-1-hydroperoxycyclohexane, alpha-cumyl hydroperoxide, methyl-alpha-cumyl hydroperoxide and isopropyl-alpha-cumyl hydroperoxide, among others.

Non-limiting examples of suitable di-(halocarbonyl) derivatives of ethylenically unsaturated dicarboxylic acids useful for preparing the novel and safe ethylenically unsaturated peroxyester compositions of this invention include fumaryl chloride (i.e., trans-1,2-di-(chlorocarbonyl)ethene), fumaryl bromide, maleoyl chloride (i.e., cis-1,2-di-(chlorocarbonyl)ethene) and itaconyl chloride (CA Service Registry Number 1931-60-8), among others. The di-(halocarbonyl) derivatives of ethylenically unsaturated dicarboxylic acids may be prepared by reacting the corresponding ethylenically unsaturated dicarboxylic acids or cyclic anhydride derivatives thereof, with acid halogenating agents, such as $PCl_3$, $PCl_5$, $POCl_3$, thionyl chloride, thionyl bromide, phosgene and benzotrichloride. Suitable optional catalysts may be used as acid halogenating catalysts, including N,N-dimethylformaide and pyridine, for example.

Non-limiting examples of suitable inorganic bases that are useful in the novel synthetic processes of this invention include sodium hydroxide, sodium carbonate, sodium hydrogen carbonate, potassium hydroxide, potassium carbonate, potassium hydrogen carbonate, calcium hydroxide, barium hydroxide, calcium carbonate and trisodium phosphate, among others.

The foregoing specific compound examples are intended to be illustrative and non-limiting, as those skilled in the art will be aware of other suitable reactive compounds.

As previously indicated, by reacting a mixture of a hydroperoxide, such as a t-alkyl hydroperoxide, and an alcohol, such as an alkanol, with a di-(halocarbonyl) compound that is a derivative of an ethylenically unsaturated dicarboxylic acid, for example, fumaryl chloride, in the presence of a base, the three-component mixture of the present invention is obtained. The peroxyester composition comprises a first component (Component I) of formula I which is derived from the alcohol; a second component (Component II) of formula II, for example OO-t-alkyl O-alkyl monoperoxyfumarate, which is derived from both the hydroperoxide and the alcohol; and a third component (Component III) of formula III, for example di-t-alkyl diperoxyfumarate, which is derived from the hydroperoxide. The following explanation is based on the exemplary use of a t-alkyl hydroperoxide as a preferred type of hydroperoxide.

If it is assumed that the reactivity of the alcohol with the di-(halocarbonyl) compound and the reactivity of the t-alkyl hydroperoxide with the di-(halocarbonyl) compound is generally the same, probability theory facilitates calculating the theoretical amount of each of the three components present in the peroxyfumarate mixture composition based upon the molar quantity of the alcohol (i.e., $m_1$) and the t-alkyl hydroperoxide (i.e., $m_2$) used in the process for preparing the novel peroxyester compositions. The molar quantity indicates the number of molecules. The important quantities for these probability calculations are: the mole fractions of the alcohol (i.e., $M_1$) and the t-alkyl hydroperoxide ($M_2$). The relationship between the molar quantity and the mole fraction is given below for the alcohol and the t-alkyl hydroperoxide:

For Alcohol:

$$M_1 = m_1/(m_1 + m_2)$$

For t-Alkyl Hydroperoxide:

$$M_2 = m_2/(m_1 + m_2)$$

Based on these equations, it should be noted that $M_1 + M_2 = 1$.

Since the mole fraction indicates the fraction of one type of molecule present as compared to all molecules, the mole fraction can be used for calculating probabilities. For example, using fumaryl chloride as an exemplary di-(halocarbonyl) compound, if 0.4 mole fraction of the alkanol is used and 0.6 mole fraction of the t-alkyl hydroperoxide is used, the probability that fumaryl chloride will initially react with the alcohol is 0.40 and the probability that fumaryl chloride will initially react with the t-alkyl hydroperoxide is 0.60. Thus, in the first step of the synthesis, 0.40 of the intermediate molecules would be alkyl trans-3-chlorocarbonyl-2-propenoate and 0.60 of the intermediate molecules would be t-alkyl peroxy-trans-3-chlorocarbonyl-2-propenoate.

In the second step of the synthesis, the alkyl trans-3-chlorocarbonyl-2-propenoate intermediate can react with the alcohol and with the t-alkyl hydroperoxide to form the dialkyl fumarate (i.e., Component I) and the OO-t-alkyl O-alkyl monoperoxyfumarate (i.e., Component II), respectively. The probability of forming the dialkyl fumarate from the alkyl trans-3-chlorocarbonyl-2-propenoate is $(0.40) \times (0.40)$ or 0.16. The probability of forming the OO-t-alkyl O-alkyl monoperoxyfumarate from the alkyl trans-3-chlorocarbonyl-2-propenoate is $(0.40) \times (0.60)$ or 0.24.

Also, in the second step of the synthesis, the t-alkyl peroxy-trans-3-chlorocarbonyl-2-propenoate intermediate can react with the alcohol and with the t-alkyl hydroperoxide to form the OO-t-alkyl O-alkyl monoperoxyfumarate (i.e., Component II) and the di-t-alkyl diperoxyfumarate (i.e., Component III), respectively. The probability of forming the OO-t-alkyl O-alkyl monoperoxyfumarate from the t-alkyl peroxy-trans-3-chlorocarbonyl-2-propenoate is $(0.60) \times (0.40)$ or 0.24. The probability of forming the di-t-alkyl diperoxyfumarate from the t-alkyl peroxy-trans-3-chloro-carbonyl-2-propenoate is $(0.60) \times (0.60)$ or 0.36.

Therefore, the probabilities of forming the three components of the peroxyester compositions of the present invention, using peroxyfumarates as non-limiting examples, when 0.40 mole fraction of the alcohol and 0.60 mole fraction of the t-alkyl hydroperoxide are used, are given below:

For Dialkyl Fumarate (Component I):

$$\text{Probability} = (M_1) \times (M_1) = (M_1)^2 = 0.16$$

For OO-t-Alkyl O-Alkyl Monoperoxyfumarate (Component II):

$$\text{Probability} = (M_1) \times (M_2) + (M_2) \times (M_1) = 2 \times M_1 M_2 = 0.48$$

For Di-t-Alkyl Diperoxyfumarate (Component III):

$$\text{Probability} = (M_2) \times (M_2) = (M_2)^2 = 0.36$$

It should be noted that the probabilities add up to 1.0, i.e.:

$$(M_1)^2 + [2 \times (M_1) \times (M_2)] + (M_2)^2 = 1.0$$

It should be noted further that the probabilities calculated represent the mole fractions of the three components of the peroxyfumarate composition. Thus, the mole fractions of the components can be calculated as follows:

Component I Mole Fraction $= (M_1)^2$
Component II Mole Fraction $= 2 \times M_1 M_2$; and
Component III Mole Fraction $= (M_2)^2$
where $M_1$ and $M_2$ are the mole fractions of the alcohol and the t-alkyl hydroperoxide, respectively.

As a further example, using 0.5 mole fraction of the alcohol and 0.5 mole fraction of the t-alkyl hydroperoxide affords the following peroxyfumarate composition:

For Dialkyl Fumarate (Component I):

$$\text{Mole Fraction} = (M_1)^2 = (0.50)^2 = 0.25$$

For OO-t-Alkyl O-Alkyl Monoperoxyfumarate (Component II):

$$\text{Mole Fraction} = 2 \times M_1 M_2 = 2 \times (0.50) \times (0.50) = 0.50$$

For Di-t-Alkyl Diperoxyfumarate (Component III):

$$\text{Mole Fraction} = (M_2)^2 = (0.50)^2 = 0.25$$

Figure 1:
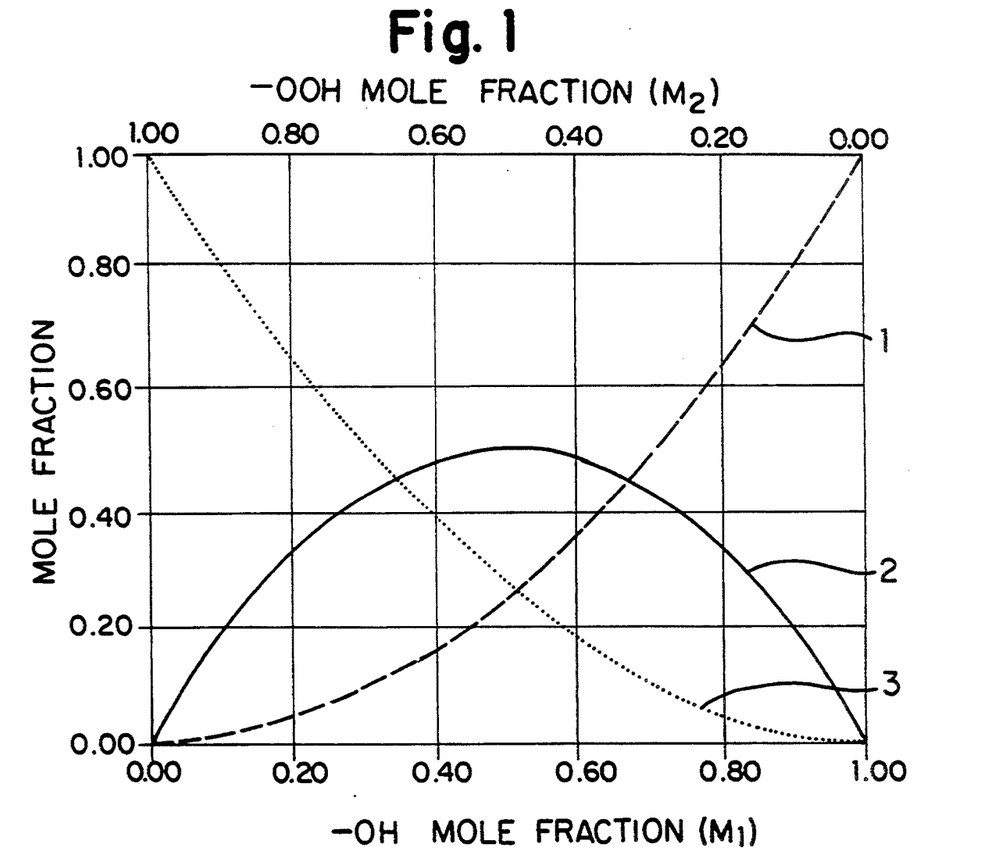
FIG. 1 is a graph depicting the expected mole fractions for the three components of the peroxyester composition of the present invention based on mole fractions of alcohol (—OH) and t-alkyl hydroperoxide (—OOH) used in the reaction with the ethylenically unsaturated di-(halocarbonyl) compound wherein the ordinate axis represents the mole fraction of components I, II or III.

FIG. 1 graphically shows the expected mole fractions for the three components in the peroxyester compositions of the present invention based on the mole fraction of the alcohol (designated generally "—OH MOLE FRACTION" in the graph) and on the mole fraction of the hydroperoxide (designated generally "—OOH MOLE FRACTION" in the graph) used in the reaction with the ethylenically unsaturated di-(halocarbonyl) compound, such as fumaryl chloride, assuming substantially identical reactivities of the alkanol and the hydroperoxide with the di-(halocarbonyl) compound. In FIG. 1, the dash line 1 corresponds to the mole fraction of Component I; the solid line 2 corresponds to the mole fraction of Component II; and the dotted line 3 corresponds to the mole fraction of Component III. At any given point along the abscissa of the graph of FIG. 1, it will be apparent that the sum of the mole fractions of the three components equals 1.00. For example, at —OH mole fraction 0.50, the peroxyester composition of the present invention comprises about 0.25 mole fraction of each of Components I and III and about 0.50 mole fraction of Component II.

Utility

Polymerization of Ethylenically Unsaturated Monomers

The ethylenically unsaturated peroxyester compositions of the present invention are effective and efficient free-radical initiators having reduced initiator requirements in free-radical polymerizations of ethylenically unsaturated monomers at suitable temperatures and pressures.

As used herein, "polymer" and its derivative terms, such as "polymerization," also includes, copolymers, terpolymers, etc., and their corresponding derivative terms.

Suitable ethylenically unsaturated monomers to be polymerized using the novel and safe ethylenically unsaturated peroxyester compositions of the present invention include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, methyl, ethyl, n-butyl, 2-hydroxyethyl, lauryl and 2-ethylhexyl acrylates and methacrylates and acrylamide and methacrylamide; maleic anhydride and itaconic anhydride; maleic, itaconic and fumaric acids and their respective esters; vinyl halogen and vinylidene dihalogen compounds, such as vinyl chloride, vinyl bromide, vinyl fluoride, vinylidene chloride and vinylidene fluoride;

perhalogen olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate, diethylene glycol bis(allyl carbonate) (also known as allyl diglycol carbonate, i.e., ADC); acrolein; methyl vinyl ketone; and mixtures thereof.

Temperatures of about 0° C. to about 250° C. and preferably about 30° C. to about 200° C., and novel peroxyester composition levels (on a pure basis) of about 0.002 to about 3% and preferably about 0.002 to about 1% by weight, more preferably, about 0.005 to about 0.7% by weight based upon monomer, are normally used in conventional polymerizations and copolymerizations of ethylenically unsaturated monomers. Suitable pressures for polymerizing the various ethylenically unsaturated monomers and mixtures thereof are the pressures typically employed in the polymerization art. The peroxyester compositions of the present invention can be used in combination with other free-radical initiators, such as those disclosed at the bottom of column 4 and the top of column 5 of U.S. Pat. No. 4,525,308. Using the novel ethylenically unsaturated peroxyester compositions of this invention in combination with the other initiators, such as those referenced in U.S. Pat. No. 4,525,308, adds flexibility to the processes of polymer producers and allows them to "fine tune" their polymerization processes.

Polymeric-Peroxides via Polymerization

The peroxyester compositions of this invention can also be homopolymerized or copolymerized with many of the above listed ethylenically unsaturated monomers at suitable temperatures and pressures in the presence or absence of conventional free-radical generating initiators to produce novel polymeric peroxides possessing at least three independent recurring units in the backbone of the polymer chain or pendant to the polymer chain:

a first recurring unit having a formula VIII:

VIII a second recurring unit having a formula IX:

IX a third recurring unit having a formula X:

X wherein $Q^1$ is a tetrayl radical having a formula XI, XII or XIII:

XI

XII

XIII where A represents the point of bonding of $Q^1$ to the carbonyl carbon of the group of formula VIII or group of formula IX or X;

D represents the point of bonding of $Q^1$ to the carbonyl carbon of the group of formula VIII or IX or group of formula X;
and R and $R^1$ are as previously defined.

Preferred are polymeric peroxides where $Q^1$ in the recurring units is formula XI.

Lower temperature free-radical initiators can be employed as the free-radical initiator to minimize decomposing the novel ethylenically unsaturated peroxyester compositions of the present invention and to maximize pendant peroxyester functionality of the resulting polymer. The procedure outlined in U.S. Pat. No. 3,536,676, which discloses di-t-alkyl diperoxyfumarates and the copolymerizations of these diperoxyfumarates with monomers, such as styrene, vinyl acetate, vinyl chloride, acrylonitrile, methyl methacrylate and butadiene, can be used wherein the novel and safe ethylenically unsaturated peroxyester compositions of the present invention are substituted for di-t-butyl diperoxyfumarate of the reference to produce the novel polymeric peroxides of the present invention.

Polymeric Peroxides via Reaction with Polymers Possessing Labile C—H Bonds

The ethylenically unsaturated peroxyester compositions of the present invention can also be reacted with polymers possessing labile C—H bonds (i.e., C—H bonds having relatively low bond dissociation energies such as below about 95 Kcal/mole) using self-activation and/or activation of the reaction with conventional peroxides or with actinic light (i.e., visible, ultraviolet, etc.) to produce novel polymeric peroxides possessing three polymer recurring units of formula VIII, formula IX and formula X pendant to the backbone of the polymers.

Suitable polymers possessing labile C—H bonds to be reacted with the novel and safe ethylenically unsaturated peroxyester compositions of the present invention to produce such novel polymeric peroxides include polyethers, such as poly(oxyethylene), poly(oxypropylene), poly(methyl vinyl ether), poly(isopropyl vinyl ether), poly(maleic anhydride-co-n-butyl vinyl ether) and poly(maleic anhydride-co-ethyl vinyl ether); unsaturated polymers, such as polybutadienes and ethylene-propylene-diene terpolymers; vinyl acetate polymers and copolymers, such as poly(vinyl acetate) and poly(ethylene-co-vinyl acetate); poly(vinyl alcohol); poly(ethylene-co-vinyl alcohol); polyacetals; polymethacrylates; polyesters; and polycarbonates.

The process for preparing the above novel polymeric peroxides described in this section comprises preparing a solution of the polymer having labile C—H bonds and the ethylenically unsaturated peroxyester compositions of the present invention in a saturated hydrocarbon solvent, such as pentane, hexane or decane or a solvent inert in the reaction, such as benzene or toluene, agitating the solution at about −20° C. to about 80° C., and either treating the solution with a conventional free-radical initiator or with light from a visible light source (e.g., a sun lamp) or with light from an ultraviolet light source. The procedure outlined in U.S. Pat. No. 3,763,112, which discloses preparing di-t-alkyl polymeric and non-polymeric diperoxyfumarate adducts via reacting a di-t-alkyl diperoxyfumarate with a compound possessing labile C—H bonds, in the presence or absence of a conventional free-radical generator and/or upon exposure to actinic light (e.g., visible or ultraviolet), can be used wherein the novel and safe ethylenically unsaturated peroxyester compositions of the present invention are substituted for the di-t-butyl diperoxyfumarate to produce novel polymeric peroxides of the present invention from polymers having labile C—H bonds. Isolating the novel polymeric peroxides by prior art methods, as set forth in U.S. Pat. No. 3,763,112, completes the preparation of the desired novel polymeric peroxides.

Curing of Unsaturated Polyester Resins

The ethylenically unsaturated peroxyester compositions of the present invention can be used to cure curable unsaturated polyester resin compositions at suitable curing temperatures in the presence of a free-radical curing agent. Unsaturated polyester resins that can be cured by the novel peroxyester compositions of this invention typically include an unsaturated polyester and one or more of an ethylenically unsaturated monomer.

The unsaturated polyesters to be cured using the peroxyester compositions of the present invention are, for example, polyesters as obtained by esterifying at least one ethylenically unsaturated dicarboxylic acid, polycarboxylic acid, anhydride or acid halide, such as maleic acid, fumaric acid, glutaconic acid, itaconic acid, mesaconic acid, citraconic acid, allylmalonic acid and tetrahydrophthalic acid with saturated and unsaturated diols and saturated and unsaturated polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,4,4-trimethyl-1,3-pentanediol, glycerol, pentaerythritol and mannitol. Mixtures of such diacids, polyacids, diols and polyols may also be used.

The ethylenically unsaturated dicarboxylic acids and ethylenically unsaturated polycarboxylic acids may be partially replaced by saturated dicarboxylic acids and polycarboxylic acids, such as adipic acid, succinic acid and sebacic acid, and by aromatic dicarboxylic acids and polycarboxylic acids, such as phthalic acid, trimellitic acid, pyromellitic acid, isophthalic acid and terephthalic acid. The unsaturated or saturated acids used may be substituted, for example, by halogen. Examples of such suitable halogenated acids are, for example, tetrachlorophthalic acid, tetrabromophthalic acid and 5,6-dicarboxy-1,2,3,4,7,7-hexachlorobicyclo(2.2.1)-2-heptene.

The other component of the unsaturated polyester resin composition, namely, the polymerizable monomer or monomers, are preferably ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate or mixtures thereof, which are copolymerizable with the aforementioned unsaturated polyesters.

Preferably, the unsaturated polyester resin composition contains, as the unsaturated polyester component, the esterification product of 1,2-propanediol, maleic anhydride and phthalic anhydride, as well as the monomer component, styrene.

Other types of unsaturated polyester resin compositions can be cured using the ethylenically unsaturated peroxyester compositions of the present invention as curing agents. These resins, generally known in the art as unsaturated vinyl ester resins, have a vinyl ester resin portion and one or more polymerizable monomer components. The vinyl ester resin component can be made by reacting a chloroepoxide, such as epichlorohydrin, with an appropriate amount of a bisphenol, such as Bisphenol-A (2,2-di-(4-hydroxyphenyl)propane), in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to about 200° C. and ethylenically unsaturated peroxyester composition levels of about 0.05% to about 5% or more, based upon weight of curable unsaturated polyester resin composition, are normally used.

The unsaturated polyester resin compositions described above can be filled with various materials, for example, sulfur, glass, carbon and boron fibers, carbon black, silicas, metal silicates, clays, metal carbonates, antioxidants (AO), heat, ultraviolet (UV) and light stabilizers, sensitizers, dyes, pigments, accelerators, metal oxides, such as zinc oxide, blowing agents and nucleating agents.

Curing of Elastomers and Crosslinking of Thermoplastic Polymers

The novel peroxyester compositions of the present invention also are useful in the curing of elastomeric compositions and the crosslinking of polymer composition by heating the elastomeric composition and/or the polymer composition at a suitable curing and crosslinking temperature in the presence of the peroxyester composition of the present invention in the presence or absence of a conventional free-radical curing and crosslinking agent.

Elastomeric resin compositions that can be cured by the novel and safe ethylenically unsaturated peroxyester compositions of the present invention include elastomers, such as ethylene-propylene copolymers (EPR), ethylene-propylenediene terpolymers (EPDM), polybutadiene (PBD), silicone rubber (SR), nitrile rubber (NR), neoprene, fluoroelastomers and ethylene-vinyl acetate copolymer (EVA).

Polymer compositions that can be crosslinked by the novel and safe ethylenically unsaturated peroxyester compositions of the present invention include polyolefinic thermoplastics, such as chlorinated polyethylene (CPE), low density polyethylene (LDPE), linear-low density polyethylene (LLDPE) and high density polyethylene (HDPE). Other crosslinkable thermoplastic polymers include PVC, polystyrene, poly(vinyl acetate), polyacrylics, polyesters, polycarbonates, etc.

Temperatures of about 80° C. to about 310° C. and ethylenically unsaturated peroxyester composition levels of about 0.1% to about 10% and preferably about 0.5% to about 5%, based upon weight of curable elastomeric resin composition or crosslinkable olefin polymer composition, are normally employed.

The curable elastomeric resin composition or crosslinkable polymer composition can be optionally filled with the materials listed above for use with the conventional unsaturated polyester resin compositions.

Modification of Polypropylene and Polypropylene Copolymers

The ethylenically unsaturated peroxyester compositions of the present invention exhibit polyolefin modification activity and are useful in processes for modifying polyolefins (e.g., the beneficial degradation of polypropylene (PP) by reducing the polymer molecular weight and narrowing the polymer molecular weight distribution of polypropylene and propylene copolymers).

The peroxyester compositions of the present invention are mixed with modifiable polypropylene polymers and heated. Temperatures of about 140° C. to about 340° C. and peroxyester composition levels of about 0.01% to about 1.0% based upon weight of modifiable propylene polymers are generally used. Optionally, up to 1% by weight of molecular oxygen based upon weight of the modifiable polypropylene polymers can be used as a modification co-catalyst.

Utility of the Novel Polymeric Peroxide Derivatives

The novel polymeric peroxide possessing the three polymer recurring units of formula VIII, formula IX and formula X of the present invention have utility in several applications. For example, the novel polymeric peroxide can be used to prepare graft copolymers via several techniques. A graft copolymer of the polymeric peroxide can be made by using the polymeric peroxide as the backbone polymer as well as the initiator, and grafting monomers onto this backbone. A graft copolymer of two or more monomers that are not the same as the monomers of the polymeric peroxide can be made by partially decomposing the polymeric peroxide in the presence of one monomer, followed by decomposing in the presence of a second monomer, and so on. The latter processes can be carried out in solution or in polymer processing equipment such as an extruder. Such graft copolymers have utility in compatibilizing homopolymer and copolymer blends and alloys.

The polymeric peroxides of the present invention can also be used in reactive processing to compatibilize polymers in situ by forming graft copolymers in polymer processing equipment, such as extruders, roll mills, etc. The polymeric peroxides can also be used to enhance the quality of an inter-penetrating polymer network (IPN) in polymer processing equipment. The polymeric peroxides of the present invention can also be used in reactive processing to enhance the impact resistance of polymer blends. The polymeric peroxides also have utility as polymeric low profile/low shrink curing agents, as self-curing polymeric systems and as self-degrading polymer systems.

Finally, the polymeric peroxides provide very useful polymer peroxide masterbatches (i.e., polymeric peroxide compositions that normally have about 5% or more of a non-polymeric organic peroxide, useful in crosslinking, curing and polymer modification applications), since the peroxide functions are covalently attached and therefore, are compatible with the polymer backbone and cannot bloom, exude or volatilize.

The present invention will now be described in more detail with reference to the following specific, non-limiting examples.

Two basic processes generally described above were used in the following examples of preparations of the novel ethylenically unsaturated peroxyester compositions of the present invention:

Procedure A—Addition of fumaryl chloride to an alcohol, t-alkyl hydroperoxide an inorganic base mixture.

Procedure B—Addition of concentrated inorganic base to a fumaryl chloride, alcohol and t-alkyl hydroperoxide mixture.

EXAMPLE 1

Preparation of a Peroxyfumarate Composition (Preparation 1) via Reaction of t-Butyl Hydroperoxide and n-Butanol with Fumaryl Chloride in the Presence of NaOH Procedure B was used in this first preparation. A 3-necked flask equipped with a stirrer, a thermometer, an addition funnel and a dry ice condenser was charged with 200 g of n-pentane, 90% t-butyl hydroperoxide (22.8 g, 0.22 mole) and n-butanol (13.3 g, 0.18 mole). 95% Fumaryl chloride (32.5 g, 0.20 mole) was then added to the stirred solution at −5° C. to 0° C. and the resulting solution was stirred vigorously. A 40% aqueous NaOH solution (50 g, 0.50 mole) was then added to the vigorously stirred solution over a period of 20 minutes and mixing was continued for 2 hours at −5° C. to 0° C. To the stirred reaction mass was then added 100 g of water, stirring was stopped, and the resulting lower aqueous layer was separated and discarded. The pentane solution of the top organic layer was then washed with buffered sodium sulfite solution, 10% NaOH solution and 3% NaHCO$_3$ solution and dried over 10% by weight of anhydrous MgSO₄. After separating the spent desiccant by filtration, the pentane was removed in vacuo leaving 38.0 g of a liquid having an active oxygen content (Act [O]) of 7.31%.

Assuming that the reactivities of t-butyl hydroperoxide and n-butanol with fumaryl chloride are the same, a theoretical composition of the resulting product can be calculated based upon the molar quantities of t-butyl hydroperoxide and n-butanol used in the reaction for preparing Preparation 1.

The theoretical mole fractions of the three components of the peroxyfumarate compositions can be calculated from the following equations:

Dialkyl Fumarate Mole Fraction (Component I) = $(M_1)^2$

OO-t-Alkyl O-Alkyl Monoperoxyfumarate Mole Fraction (Component II) = $2 \times M_1 M_2$ Di-t-alkyl Diperoxyfumarate Mole Fraction (Component III) = $(M_2)^2$ where $M_1$ is the mole fraction of the alcohol and $M_2$ is the mole fraction of the t-alkyl hydroperoxide. $M_1$ and $M_2$ are determined from the following Equations A and B:

$$M_1 = m_1/(m_1+m_2) \quad \text{Equation A}$$

$$M_2 = m_2/(m_1+m_2) \quad \text{Equation B}$$

where $m_1$ and $m_2$ are the molar quantities of the alcohol and t-alkyl hydroperoxide, respectively, used in the reaction.

Thus, based upon using 0.18 mole ($m_1$) of n-butanol, 0.22 mole ($m_2$) of t-butyl hydroperoxide and 0.20 mole of fumaryl chloride in the above preparation, the theoretical expected mole fractions of the composition components are as follows:

Di-n-Butyl Fumarate Mole Fraction (Component I) = 0.203

OO-t-Butyl O-n-Butyl Monoperoxyfumarate Mole Fraction (Component II) = 0.495

Di-t-Butyl Diperoxyfumarate) Mole Fraction (Component III) = 0.302

Since 0.20 mole of fumaryl chloride was used in the above preparation, the molar and gram quantities of the components produced are calculated as follows:

Di-n-Butyl Fumarate (Component I, Formula Weight (FW) = 228.3, Theoretical Act [O] = 0.00%)

(0.203 mole) × (0.20) = 0.0406 mole, 9.27 g Act [O] contribution = 0.00 g

OO-t-Butyl O-n-Butyl Monoperoxyfumarate (Component II, FW = 244.3, Theoretical Act [O] = 6.55%)

(0.495 mole) × (0.20) = 0.0990 mole, 24.19 g Act [O] contribution = 1.58 g

Di-t-Butyl Diperoxyfumarate (Component III, FW = 260.3, Theoretical Act [O] = 12.29%)

(0.302 mole) × (0.20) = 0.0604 mole, 15.72 g Act [O] contribution = 1.93 g

Therefore, the theoretical yield of the peroxyfumarate composition of Preparation 1 = (9.27 g + 24.19 g + 15.72 g) = 49.2 g Theoretical Act[O] = (0.00 g + 1.58 g + 1.93 g) = 3.51 g Theoretical Act [O] = (3.51 g/49.2 g) × 100 = 7.13%

Since the actual yield and the actual Act[O] were 38.0 g and 7.31%, respectively, the uncorrected yield was 77.2% and the yield corrected for Act[O] (i.e., the corrected yield) was 79.1%. The higher than expected Act[O] indicated that t-butyl hydroperoxide was somewhat more reactive towards fumaryl chloride than the n-butanol was. The first peroxyfumarate composition (Preparation 1) was found to have a half-life of 19.0 hours at 100° C. in alpha-methylstyrene based on conventional determination procedures.

EXAMPLE 2

Preparation of a Peroxyfumarate Composition (Preparation 2) via Reaction of t-Butyl Hydroperoxide and n-Butanol with Fumaryl Chloride in the Presence of NaOH In a second preparative process also using Procedure B, as described in Example 1, 0.40 mole of fumaryl chloride, 0.45 mole of n-butanol and 0.44 mole of t-butyl hydroperoxide were reacted as above. After a similar work-up, 81.0 g of a liquid peroxyfumarate composition, Preparation 2, was obtained having an Act[O] content of 6.73%.

Based upon using 0.45 mole ($m_1$) of n-butanol, 0.44 mole ($m_2$) of t-butyl hydroperoxide and 0.40 mole of fumaryl chloride in Preparation 2, the theoretical expected mole fractions of the composition components are as follows:

Di-n-Butyl Fumarate Mole Fraction (Component I) = 0.256

OO-t-Butyl O-n-Butyl Monoperoxyfumarate) Mole Fraction (Component II) = 0,500

Di-t-Butyl Diperoxyfumarate) Mole Fraction (Component III) = 0.244

Since 0.40 mole of fumaryl chloride was used in this second preparation, the molar and gram quantities of the components produced are:

Di-n-Butyl Fumarate (Component I FW = 228.3, Theoretical Act [O] = 0.00%)

(0.256 mole) × (0.40) = 0.1024 mole, 23.38 g Act [O] contribution = 0.00 g

OO-t-Butyl O-n-Butyl Monoperoxyfumarate (Component II FW = 244.3, Theoretical Act[O] = 6.55% (0.500 mole) × (0.40) = 0.2000 mole, 48.86 g Act [O] contribution = 3.20 g Di-t-Butyl Diperoxyfumarate (Component III FW = 260.3, Theoretical Act[O] = 12.29%) (0.244) × (0.40) = 0.0976 mole, 25.41 g Act[O] contribution = 3.12 g Therefore, the theoretical yield of the peroxyfumarate composition of Preparation 2 = (23.38 g + 48.86 g + 25.41 g) = 97.6 g Theoretical Act[O] = (0.00 g + 3.20 g + 3.12 g) = 6.32 g Theoretical Act[O] = (6.32 g/97.6 g) × 100 = 6.48%

Since the actual yield and the actual % Act[O] for Preparation 2 were 81.0 g and 6.73%, respectively, the uncorrected yield was 83.0% and the yield corrected for Act[O] (i.e., the corrected yield) was 86.2%. The higher than expected Act[O] indicated that t-butyl hydroperoxide was somewhat more reactive towards fumaryl chloride than the n-butanol was.

EXAMPLE 3

Preparation of a Peroxyfumarate Composition (Preparation 3) via Reaction of t-Butyl Hydroperoxide and n-Butanol with Fumaryl Chloride in the Presence of NaOH Procedure A was used to prepare a third liquid peroxyfumarate composition (Preparation 3). A jacketed reactor equipped with a stirrer, a thermometer and an addition funnel was charged with 125 mL of n-pentane and a 25% aqueous NaOH solution .(43.2 g, 0.27 mole). To this stirred mixture at 5° C. was added aqueous 70% t-butyl hydroperoxide (9.0 g, 0.07 mole) and n-butanol (11.1 g, 0.15 mole). Addition of 3 g of water was required to keep the sodium salt of t-butyl hydroperoxide in solution. The resulting vigorously stirred, two-phase liquid mixture was cooled to −5° C. and to it was added 94% fumaryl chloride (16.3 g, 0.10 mole) was added over a period of 30 minutes. Mixing was continued for an additional 90 minutes at −5° C. to 0° C. Stirring was stopped and the resulting lower aqueous layer was separated and discarded. The top pentane solution was then washed with 50 mL of aqueous buffered sodium sulfite, 50 mL of 10% aqueous NaOH and twice with 50 mL portions of aqueous 3% $NaHCO_3$. The pentane layer was then dried over 10% by weight of anhydrous $MgSO_4$. After separating the spent desiccant by filtration, the pentane was removed in vacuo leaving 19.5 g of a liquid product having an Act[O] content of 4.24%.

Assuming equal reactivities of n-butanol and t-butyl hydroperoxide with fumaryl chloride, the theoretical product composition for Preparation 3 should be 0.0465 mole of di-n-butyl fumarate (Component I), 0.0434 mole of OO-t-butyl O-n-butyl monoperoxyfumarate (Component II) and 0.0101 mole of di-t-butyl diperoxyfumarate (Component III). Based on these molar quantities, the theoretical yield was 23.8 g and the theoretical Act[O] was 4.27%. Therefore, for Preparation 3, the uncorrected yield was 81.9% and the yield corrected for Act[O] (i.e., the corrected yield) was 81.3%.

The similar Act[O] levels indicated that n-butanol and t-butyl hydroperoxide had about the same activity toward fumaryl chloride in Preparation 3.

EXAMPLE 4

Preparation of a Peroxyfumarate Composition (Preparation 4) via Reaction of t-Butyl Hydroperoxide and n-Butanol with Fumaryl Chloride in the Presence of NaOH Procedure A was again used to prepare a liquid peroxyfumarate composition (Preparation 4). A jacketed reactor equipped with a stirrer, a thermometer and an addition funnel was charged with 125 mL of n-pentane and a 25% aqueous NaOH solution (43.2 g, 0.27 mole). To this stirred mixture at 5° C. was added aqueous 70% t-butyl hydroperoxide (16.7 g, 0.13 mole) and n-butanol (6.7 g, 0.09 mole). Addition of 3 g of water was required to keep the sodium salt of t-butyl hydroperoxide in solution. The resulting vigorously stirred two phase liquid mixture was cooled to −5° C. and 94% fumaryl chloride (16.3 g, 0.10 mole) was added over a period of 30 minutes. Mixing was continued for an additional 45 minutes at −5° C. to 0° C. Stirring was stopped and the resulting lower aqueous layer was separated and discarded. The top pentane solution was then washed with 50 mL of aqueous buffered sodium sulfite, 50 mL of 10% aqueous NaOH and twice with 50 mL portions of aqueous 3% $NaHCO_3$. The pentane layer was then dried over 10% by weight of anhydrous $MgSO_4$. After separating the spent desiccant by filtration, the pentane was removed in vacuo leaving 20.2 g of a liquid product having an Act[O] content of 7.25%.

Assuming equal reactivities of n-butanol and t-butyl hydroperoxide with fumaryl chloride, the theoretical product composition for Preparation 4 should be 0.0167 mole of di-n-butyl fumarate (Component I), 0.0483 mole of OO-t-butyl O-n-butyl monoperoxyfumarate (Component II) and 0.0349 mole of di-t-butyl diperoxyfumarate (Component III). Based on these molar quantities, the theoretical yield was 24.7 g and the theoretical Act[O] was 7.65%. Therefore, for Preparation 4, the uncorrected yield was 81.7% and the yield corrected for Act[O] (i.e., the corrected yield) was 77.5%.

EXAMPLE 5

Preparation of a Peroxyfumarate Composition (Preparation 5) via Reaction of t-Butyl Hydroperoxide and n-Butanol with Fumaryl Chloride in the Presence of NaOH Procedure A was used again to prepare a liquid peroxyfumarate composition (Preparation 5). A jacketed reactor equipped with a stirrer, a thermometer and an addition funnel was charged with 833 g of hexane and a 25% aqueous NaOH solution (432.0 g, 2.70 moles). To this stirred mixture at 5° C. was added aqueous 69.2% t-butyl hydroperoxide (143.0 g, 1.10 moles), n-butanol (82.0 g, 1.10 moles) and 30 g of water. The resulting vigorously stirred two phase liquid mixture was cooled to −10° C. and 94% fumaryl chloride (163.0 g, 1.00 mole) was added over a period of 30 minutes at −10° C. to −5° C. Mixing was continued for an additional 10 minutes at −5° C. Stirring was stopped and the resulting lower aqueous layer was separated and discarded. The top hexane solution was then treated as were the pentane layers in Preparations 3 and 4. After drying over 10% by weight of anhydrous $MgSO_4$ and separating the spent desiccant by filtration, the hexane was removed in vacuo leaving 204.0 g of a liquid product having an Act[O] content of 6.76%.

Assuming equal reactivities of n-butanol and t-butyl hydroperoxide with fumaryl chloride, the theoretical product composition for Preparation 5 should be 0.25 mole of di-n-butyl fumarate (Component I), 0.50 mole of OO-t-butyl O-n-butyl monoperoxyfumarate (Component II) and 0.25 mole of di-t-butyl diperoxyfumarate (Component III). Based on these molar quantities, the theoretical yield was 244.3 g and the theoretical Act[O] was 6.55%. Therefore, for Preparation 5, the uncorrected yield was 83.5% and the yield corrected for Act[O] (i.e., the corrected yield) was 86.2%.

A differential scanning calorimetry (DSC) scan of peroxyfumarate Preparation 5 showed a peroxide decomposition exotherm at 127° C. and a second, lesser peroxide exotherm centered at about 160° C. The total energy released from these peroxide decomposition exotherms was 1278 Joules per gram (J/g). However, not all of the exothermic energy was due to peroxide decomposition. Some of this exothermic energy was due to polymerization of Preparation 5 and/or decomposition products having polymerizable carbon-carbon double bonds. This polymerization energy was estimated to be about 266 J/g for this composition based on a heat of polymerization of 65 kJ/mole for diethyl fumarate, a model compound, as set forth in *Polymer Handbook*, 2nd Ed., John Wiley & Sons, New York, p. 425 (1975). Therefore, the actual energy produced in the decomposition of peroxyfumarate Preparation 5 was about 1,012 J/g.

EXAMPLE 6

Preparation of Di-t-butyl Diperoxyfumarate (Preparation 6) via Reaction of t-Butyl Hydroperoxide with Fumaryl Chloride in the Presence of NaOH Procedure B was employed in this preparation of di-t-butyl diperoxyfumarate (Preparation 6), a known diperoxide compound. A 3-necked flask equipped with a stirrer, a thermometer, an addition funnel and a dry ice condenser was charged with 100 g of n-pentane and 90% t-butyl hydroperoxide (50.2 g, 0.50 mole) (pre-dried over $MgSO_4$). 95% Fumaryl chloride (32.5 g, 0.20 mole) was then added to the stirred solution at $-5°$ C. to $0°$ C. A 50% aqueous NaOH solution (36 g, 0.45 mole) was then added to the vigorously stirred solution over a period of 20 minutes and mixing was continued for 2 hours at $-5°$ C. to $0°$ C. To the stirred reaction mass was then added 100 g of water and 100 g of pentane, stirring was stopped, and the resulting lower aqueous layer was separated and discarded. The top pentane solution was then washed with buffered sodium sulfite solution, 10% NaOH solution and 3% $NaHCO_3$ solution. The pentane solution was then dried over 10% by weight of anhydrous $MgSO_4$. After separating the spent desiccant by filtration, the pentane solution was cooled to $-45°$ C. and a solid product precipitated. The solid product was separated by filtration, washed with cold pentane and dried to give 26.0 g (49.9% of theory, uncorrected) of a solid, with a melting point (mp) of $29°-31°$ C., having an Act[O] content of 12.22%. Based upon the theoretical active oxygen content of 12.29% for di-t-butyl diperoxyfumarate, the assay of the product, Preparation 6, was 99.4% and the corrected yield was 49.6%.

EXAMPLE 7

Preparation of Di-t-butyl Diperoxyfumarate (Preparation 7) via Reaction of t-Butyl Hydroperoxide with Fumaryl Chloride in the Presence of NaOH This example sets forth an alternative preparation of the known compound di-t-butyl diperoxyfumarate (Preparation 7) using Procedure A. A jacketed reactor equipped with a stirrer, a thermometer and an addition funnel was charged with 125 mL of n-pentane and a 25% aqueous NaOH solution (43.0 g, 0.27 mole). The mixture was stirred. To this stirred mixture maintained at $10°$ C., 87.5% t-butyl hydroperoxide (22.6 g, 0.22 mole) was added. Addition of 20 g of water was required to keep the sodium salt of t-butyl hydroperoxide in solution. The resulting vigorously stirred two phase liquid mixture was cooled to $-3°$ C. and 94% fumaryl chloride (16.3 g, 0.10 mole) was added over a period of 30 minutes. Mixing was continued for an additional 90 minutes at $-3°$ C. to $0°$ C. Stirring was stopped and the resulting lower aqueous layer was separated and discarded. The top pentane solution was then washed with 50 mL of aqueous buffered sodium sulfite, 50 mL of 10% aqueous NaOH and twice with 50 mL portions of aqueous 3% $NaHCO_3$ solution. The pentane solution was then dried over 10% by weight of anhydrous $MgSO_4$. After separating the spent desiccant by filtration, the pentane was removed in vacuo leaving 17.8 g (68.5% of theory, uncorrected) of a solid product having an Act [O] content of 11.81%. Based on the theoretical active oxygen content of 12.29% for di-t-butyl diperoxyfumarate, the assay of the product, Preparation 7, was 96.1% and the corrected yield was 65.8%.

The enhanced yield of the peroxyester composition containing di-t-butyl diperoxyfumarate as Component III of Examples 1–5 compared to the yield of the present invention is demonstrated in the following Table 2:

TABLE 2

| Peroxyfumarate | Corrected Yield, %* |
|---|---|
| Novel Peroxyfumarates | |
| Preparation 1 | 79.1 |
| Preparation 2 | 86.2 |
| Preparation 3 | 81.3 |
| Preparation 4 | 77.5 |
| Preparation 5 | 86.2 |
| Average Novel Peroxyfumarates | 82.1 |
| Prior Art Di-t-butyl Diperoxyfumarate | |
| Preparation 6 | 49.6 |
| Preparation 7 | 65.8 |
| Average Prior Art | 57.7 |

*Based on fumaryl chloride

The results show that the unsaturated peroxyester compositions of this invention were obtained in significantly higher corrected yields than were the di-t-alkyl diperoxyfumarates of the prior art.

EXAMPLE 8

Preparation of a Peroxyfumarate Composition (Preparation 8) via Reaction of t-Amyl Hydroperoxide and Methanol with Fumaryl Chloride in the Presence of KOH Procedure B was used in this preparation. A 3-necked flask equipped with a stirrer, a thermometer, an addition funnel and a dry ice condenser was charged with 200 g of n-pentane, 87.3% t-amyl hydroperoxide (26.2 g, 0.22 mole) and methanol (5.8 g, 0.18 mole). 95% Fumaryl chloride (32.5 g, 0.20 mole) was then added to the stirred solution at $-5°$ C. to $0°$ C. A 45% aqueous KOH solution (62.4 g, 0.50 mole) and 7.5 g of water were then added to the vigorously stirred solution over a period of 30 minutes and mixing was continued for 3 hours at $-5°$ C. to $0°$ C. To the stirred reaction mass was added 100 g of water, stirring was stopped and the resulting lower aqueous layer was separated and discarded. The top pentane solution was then washed with buffered sodium sulfite solution, 10% NaOH solution and 3% $NaHCO_3$ solution. The pentane layer was then dried over 10% by weight of anhydrous $MgSO_4$. After separating the spent desiccant by filtration, the pentane was removed in vacuo leaving 34.0 g of a liquid having an Act[O] content of 8.33%.

Assuming equal reactivities of methanol and t-amyl hydroperoxide with fumaryl chloride, the theoretical product composition for this example (Preparation 8) should be 0.0406 mole of dimethyl fumarate (Component I), 0.0990 mole of OO-t-amyl O-methyl monoperoxyfumarate (Component II) and 0.0604 mole of di-t-amyl diperoxyfumarate (Component III). Based upon these molar quantities, the theoretical yield was 44.7 g and the theoretical Act[O] was 7.87%. Therefore, for this example, the uncorrected yield was 76.1% and the yield corrected for Act[O] (i.e., the corrected yield) was 80.5%.

The higher than expected Act[O] indicated that t-amyl hydroperoxide was somewhat more reactive towards fumaryl chloride than methanol was.

EXAMPLE 9

Preparation of Di-t-amyl Diperoxyfumarate (Preparation 9) via Reaction of t-Amyl Hydroperoxide with Fumaryl Chloride in the Presence of NaOH Procedure B was used in this preparation of di-t-amyl diperoxyfumarate, a known compound (Preparation 9). A 3-necked flask equipped with a stirrer, a thermometer, an addition funnel and a dry ice condenser was charged with 100 g of n-pentane and 87% t-amyl hydroperoxide (53.8 g, 0.45 mole). 95% Fumaryl chloride (32.5 g, 0.20 mole) was then added to the stirred solution at −15° C. A 50% aqueous NaOH solution (33 g, 0.41 mole) was then added to the vigorously stirred solution over a period of 30 minutes and mixing was continued for 2 hours at −15° C. to −12° C. To the stirred reaction mass was then added 100 g of water and 100 g of pentane, stirring was stopped and the resulting lower aqueous layer was separated and discarded. The top pentane solution was then washed with buffered sodium sulfite solution, 5% NaOH solution and 3% NaHCO$_3$ solution. The pentane layer was then dried over 10% by weight of anhydrous MgSO$_4$. After separating the spent desiccant by filtration, the pentane solution was cooled to −40° C. and a solid product precipitated. The solid product was separated by filtration, washed with cold pentane and dried to give 31.0 g (53.7% of theory, uncorrected) of a solid, with a mp of 31°–33° C., having an Act[O] content of 10.92%. Based on the theoretical active oxygen content of 11.10% for di-t-amyl diperoxyfumarate, the assay of the product, Preparation 9, was 98.4% and the corrected yield was 52.8%.

EXAMPLE 10

Preparation of a Peroxyfumarate Composition (Preparation 10) via Reaction of 1-Ethyl-1-methylpropyl Hydroperoxide and Methanol with Fumaryl Chloride in the Presence of NaOH Procedure B was used in this preparation. A 3-necked flask equipped with a stirrer, a thermometer, an addition funnel and a dry ice condenser was charged with 300 g of n-pentane, 83.7% 1-ethyl-1-methylpropyl hydroperoxide (14.2 g, 0.1.2 mole) and methanol (3.2 g, 0.10 mole). 95% Fumaryl chloride (16.2 g, 0.10 mole) was then added to the stirred solution at −10° C. to −5° C. A 50% aqueous NaOH solution (20 g, 0.25 mole) and 2.0 g of water were then added to the vigorously stirred solution over a period of 10 minutes and mixing was continued for 10 minutes at −10° C. to −5° C. To the stirred reaction mass was then added 100 g of water, stirring was stopped, and the resulting lower aqueous layer was separated and discarded. The top pentane solution was then washed with buffered sodium sulfite solution, 3% NaOH solution and 3% NaHCO$_3$ solution. The pentane layer was then dried over 10% by weight of anhydrous MgSO$_4$. After separating the spent desiccant by filtration, the pentane was removed in vacuo leaving 17.0 g of a liquid having an Act[O] content of 7.42%.

Assuming equal reactivities of methanol and 1-ethyl-1-methylpropyl hydroperoxide with fumaryl chloride, the theoretical product composition for this example (Preparation 10) should be 0.0207 mole of dimethyl fumarate (Component I), 0.0496 mole of OO-(1-ethyl-1-methylpropyl) O-methyl monoperoxyfumarate (Component II) and 0.0297 mole of di-(1-ethyl-1-methylpropyl) diperoxyfumarate (Component III). Based on these molar quantities, the theoretical yield was 23.8 g and the theoretical Act[O] was 7.33%. Therefore, for this example, the uncorrected yield of the product, Preparation 10, was 71.4% and the yield corrected for Act[O] (i.e., the corrected yield) was 72.3%.

The higher than expected Act[O] indicated that 1-ethyl-1-methylpropyl hydroperoxide was somewhat more reactive towards fumaryl chloride than methanol was.

EXAMPLE 11

Preparation of Di-(1-ethyl-1-methylpropyl) Diperoxyfumarate (Preparation 11) via Reaction of 1-Ethyl-1-methylpropyl Hydroperoxide with Fumaryl Chloride in the Presence of NaOH Procedure B was used in this preparation of di-(1-ethyl-1-methylpropyl) diperoxyfumarate (Preparation 11). A 3-necked flask equipped with a stirrer, a thermometer, an addition funnel and a dry ice condenser was charged with 220 g of n-pentane and 83.7% 1-ethyl-1-methylpropyl hydroperoxide (45.2 g, 0.32 mole). 95% Fumaryl chloride (26.1 g, 0.16 mole) was then added to the stirred solution at −10° C. to −5° C. A 50% aqueous NaOH solution (32 g, 0.40 mole) and 3.2 g of water were then added to the vigorously stirred solution over a period of 10 minutes and mixing was continued for 5 minutes at −10° C. to −5° C. To the stirred reaction mass was added 200 g of water, stirring was stopped and the resulting lower aqueous layer was separated and discarded. The top pentane solution was then washed with buffered sodium sulfite solution, 5% Na$_2$CO$_3$ solution and 3% NaHCO$_3$ solution. The pentane layer was then dried over 10% by weight of anhydrous MgSO$_4$. After separating the spent desiccant by filtration, the pentane solution was cooled to −20° C. and a solid product precipitated. The solid product was separated by filtration, washed with cold pentane and dried to give 37.0 g (73.1% of theory, uncorrected) of a solid, with amp of 23°–25° C., having an Act[O] content of 8.40%. Based on the theoretical Act[O] of 10.12% for di-(1-ethyl-1-methylpropyl)diperoxyfumarate, the assay of the product, Preparation 11, was 83.0% and the corrected yield was 60.7%.

EXAMPLE 12

Preparation of a Peroxyfumarate Mixture Composition (Preparation 12) via Reaction of 1,1,3,3-Tetramethylbutyl Hydroperoxide and Methanol with Fumaryl Chloride in the Presence of NaOH Procedure B was used in this preparation. A 3-necked flask equipped with a stirrer, a thermometer, an addition funnel and a dry ice condenser was charged with 300 g of n-pentane, 90.2% 1,1,3,3-tetramethylbutyl hydroperoxide (17.8 g, 0.11 mole) and methanol (3.2 g, 0.10 mole). 95% Fumaryl chloride (16.1 g, 0.10 mole) was then added to the stirred solution at −10° C. to −5° C. A 50% aqueous NaOH solution (32 g, 0.40 mole) and 3.2 g of water were then added to the vigorously stirred solution over a period of 10 minutes and mixing was continued for 5 minutes at −10° C. to −5° C. To the stirred reaction mass was then added 100 g of water, stirring was stopped and the resulting lower aqueous layer was separated and discarded. The top pentane solution was then washed with buffered sodium sulfite solution, 5% aqueous Na$_2$CO$_3$ solution, 3% NaHCO$_3$ solution and water. The pentane layer was then dried over 10% by weight of anhydrous MgSO4. After separating the spent desiccant by filtration, the pentane was removed in vacuo, leaving 21.0 g of a liquid having an Act[O] content of 6.29%. Assuming equal reactivities of methanol and 1,1,3,3-tetramethylbutyl hydroperoxide with fumaryl chloride, the theoretical product composition for this example (Preparation 12) should be 0.0227 mole of dimethyl fumarate (Component I), 0.0499 mole of OO-(1,1,3,3-tetramethylbutyl) O-methyl monoperoxyfumarate (Component II) and 0.0274 mole of di-(1,1,3,3-tetramethylbutyl) diperoxyfumarate (Component III). Based on these molar quantities, the theoretical yield was 26.4 g and the theoretical Act[O] was 6.35%. Therefore, for this example, the uncorrected yield was 79.5% and the yield corrected for Act[O] (i.e., the corrected yield) was 78.8%. The expected Act[O] and the actual Act[O] were essentially the same, indicating that 1,1,3,3-tetramethylbutyl hydroperoxide and methanol had similar reactivities with fumaryl chloride.

EXAMPLE 13

Preparation of Di-(1,1,3,3-tetramethylbutyl) Diperoxyfumarate (Preparation 13) via Reaction of 1,1,3,3-Tetramethylbutyl Hydroperoxide with Fumaryl Chloride in the Presence of NaOH Procedure B was used in this preparation of di-(1,1,3,3-tetramethylbutyl) diperoxyfumarate, Preparation 13. A 3-necked flask equipped with a stirrer, a thermometer, an addition funnel and a dry ice condenser was charged with 300 g of n-pentane and 90% 1,1,3,3-tetramethylbutyl hydroperoxide (52.1 g, 0.32 mole). 95% Fumaryl chloride (26.1 g, 0.16 mole) was then added to the stirred solution at −10° C. to −5° C. A 50% aqueous NaOH solution (32 g, 0.40 mole) and 3.2 g of water were then added to the vigorously stirred solution over a period of 10 minutes and mixing was continued for 10 minutes at −10° C. to −5° C. To the stirred reaction mass was then added 100 g of water, stirring was stopped and the resulting lower aqueous layer was separated and discarded. The top pentane solution was then washed with buffered sodium sulfite solution and 3% NaHCO3 solution. The pentane layer was then dried over 10% by weight of anhydrous MgSO4. After separating the spent desiccant by filtration, the pentane was removed in vacuo leaving 51.0 g (85.6% of theory, uncorrected) of a liquid having an Act[O] content of 7.17%. Based on the theoretical active oxygen content of 8.60% for di-(1,1,3,3-tetramethylbutyl) diperoxyfumarate, the assay of the product was 83.4% and the corrected yield was 71.3%. The yields of the peroxyfumarate compositions of the present invention, namely Preparations 8, 10 and 12, and the corresponding diperoxides, namely, di-t-amyl diperoxyfumarate (Preparation 9), di-(1-ethyl-1-methylpropyl) diperoxyfumarate (Preparation 11), and di-(1,1,3,3-tetramethylbutyl) diperoxyfumarate (Preparation 13), are summarized below in Table 3:

TABLE 3

| Peroxyfumarate Preparations | | |
|---|---|---|
| Peroxyfumarate | | Corrected Yield, % |
| Preparation 8 | Invention | 80.5 |
| Preparation 9 | Diperoxyfumarate | 52.8 |
| Preparation 10 | Invention | 72.3 |
| Preparation 11 | Diperoxyfumarate | 60.7 |
| Preparation 12 | Invention | 78.8 |

TABLE 3-continued

| Peroxyfumarate Preparations | | |
|---|---|---|
| Peroxyfumarate | | Corrected Yield, % |
| Preparation 13 | Diperoxyfumarate | 71.3 |

The yield results, as tabulated above, and taken together with the yield results of Table 2, indicate that the novel and safe ethylenically unsaturated peroxyester compositions of the present invention are obtained in significantly better corrected yields than are the corresponding di-t-alkyl diperoxyfumarates derived from the same t-alkyl hydroperoxide.

EXAMPLE 14

Preparation of a Styrene-Peroxyfumarate Copolymer: poly[styrene-co-(di-n-butyl fumarate)-co-(OO-t-butyl O-n-butyl monoperoxyfumarate)-co-(di-t-butyl diperoxyfumarate)]

In this example, peroxyfumarate composition Preparation 5 and styrene were used as co-monomers in a copolymerization in which t-butyl peroxypivalate was used as a low temperature free-radical initiator.

A 3-necked flask equipped with a magnetic stirring bar, a nitrogen inlet, a thermometer, an addition funnel and a condenser was charged with 100 g of xylenes, styrene monomer (30.0 g, 0.283 mole) and peroxyfumarate composition of Preparation 5 (15.0 g, 0.0614 mole, average molecular weight (MW)=244 g/mole) at 20°-25° C. The air above the solution was displaced with dry nitrogen gas. A solution of 10 g of xylenes and 75% t-butyl peroxypivalate in odorless mineral spirits (Lupersol 11 TM, manufactured by the Organic Peroxides Division of Elf Atochem North America, Inc.) (0.9 g, 0.0039 mole) was rapidly added to the stirred solution at 20°-25° C. The resulting solution was then heated to 55° C. and held at 55° C. for 8 hours under dry nitrogen gas. The solution was then poured into 500 mL of vigorously stirred methanol. No solid polymer formed and the volatile material (i.e, xylenes, styrene and methanol) was removed in vacuo. After concentrating the solution, a gummy solid polymer was obtained.

This solid was extracted 6 times at room temperature with 200 mL portions of methanol to remove residual styrene, xylenes, odorless mineral spirits and t-butyl peroxypivalate and any unreacted components from the peroxyfumarate composition Preparation 5. These extractions were carried out in a shallow glass bake pan. A spatula was used to stir the polymer in the methanol. After the last extraction, the solid polymer was dried in a well ventilated hood at room temperature over a 24-hour period. 9.7 g (21.6% of theory, uncorrected) of a white solid polymer was obtained having an Act[O] content of 2.22%. Based upon the quantities of styrene and peroxyfumarate composition Preparation 5 that were used, the theoretical Act[O] for the polymeric peroxide was 2.25%. A DSC scan indicated a peroxide decomposition exotherm at about 150° C. and a peroxide decomposition energy of 366 J/g. Based on a peroxide decomposition energy of 1,012 J/g for peroxyfumarate composition Preparation 5 (see Example 5), the theoretical peroxide decomposition energy for the polymeric peroxide of the present example was 337 J/g.

The Act[O] data and the DSC data for the product of this example confirm that the desired novel polymeric peroxide named in the caption of this Example was obtained by copolymerizing peroxyfumarate composition Preparation 5 and styrene monomer in the presence of t-butyl peroxypivalate. This example illustrates the copolymerization of a novel and safe ethylenically unsaturated peroxyester composition, i.e., Preparation 5, with an ethylenically unsaturated monomer, i.e., styrene, to produce a novel polymeric peroxide.

EXAMPLE 15

Preparation of an Ethylene/Vinyl Acetate Copolymer Grafted with Peroxyfumarate Composition Preparation 5

In this example, peroxyfumarate composition Preparation 5 was grafted onto an ethylene/vinyl acetate copolymer using actinic light from a sun lamp for initiating the grafting reaction to produce a peroxyfumarate mixture grafted ethylene/vinyl acetate copolymer.

A jacketed 3-necked flask equipped with a mechanical stirrer, a nitrogen inlet, a thermometer, an addition funnel and a condenser was charged with 130–140 mL of toluene and 10 g of an ethylene/vinyl acetate copolymer having a 40% vinyl acetate content (VYNATHENE ™ Vinyl Acetate-Ethylene Copolymer, Grade EY 901, manufactured by U.S.I. Chemicals Co.). The mixture was stirred at room temperature until the ethylene/vinyl acetate copolymer was solubilized. Peroxyfumarate composition Preparation 5 (2.4 g, 0.010 mole, avg. MW=244 g/mole) was then added over a period of 2 hours while the solution was irradiated with a sun lamp at 25°–30° C. The resulting solution was further irradiated with a sun lamp at 20°–25° C. for an additional 2 hours. The resulting solution was then poured into about 1500 mL of n-pentane and the resulting rubbery polymer was removed from the spent n-pentane. The rubbery polymer was subsequently soaked in 500 mL of n-pentane for 1 hour at 20°–25° C. after which the spent pentane was removed. This soaking/extraction procedure was repeated three additional times to remove unreacted peroxyfumarate composition Preparation 5 and toluene. Subsequent complete evaporation of the combined pentane extracts yielded about 2.0 g of liquid which was primarily identified as Preparation 5, per its infrared spectrum. The rubbery product was dried in a forced air hood, cut into small pieces and dried in a vacuum oven at 30° C. for 2 hours. 9.4 g (75.8% of theory, uncorrected) of a rubbery polymer was obtained.

A DSC scan of the graft peroxy-copolymer product showed a definite peroxide decomposition exotherm at about 162° C. and a peroxide decomposition energy of 11 J/g. The total peroxide decomposition energy for the product obtained was 103 J (the product of 11 J/g and 9.4 g of product). Based on a peroxide decomposition energy of 1,012 J/g (246,900 J/mole) for peroxyfumarate composition Preparation 5 (see Example 5), the 9.4 g of peroxy copolymer product of the present example contained about 0.10 g (i.e., 103 J divided by 1,012 J/g) of grafted peroxyfumarate composition Preparation 5. The Act[O] content based on the total peroxide decomposition energy of the product peroxy-copolymer of the present example was 0.07%.

The DSC data for the product of this example and subsequent calculations based on DSC data confirm that the desired novel grafted peroxy-copolymer was obtained by grafting peroxyfumarate composition Preparation 5 onto an ethylene/vinyl acetate copolymer.

This example illustrated the grafting of a novel and safe ethylenically unsaturated peroxyester composition, i.e., Preparation 5, onto a polymer with labile C—H bonds, i.e., an ethylene/vinyl acetate copolymer, to produce a novel polymeric peroxide.

EXAMPLE 16

Comparison of the Safety Characteristics of Peroxyfumarate Composition Preparation 1 with the Safety Characteristics of Di-t-Butyl Diperoxyfumarate Preparation 6

Various safety tests were conducted on peroxyfumarate composition Preparation 1 and on di-t-butyl diperoxyfumarate Preparation 6 of Example 6. The procedures used in the Shock Sensitivity test, the modified Trauzl test and the Rapid Heat test and the interpretation of the results are described by Mageli in J. Chem. Ed., 48, p. A451 (1971). The results are summarized in Table 4 and show that Preparation 1, a peroxyfumarate composition of the present invention, was significantly safer and less hazardous than the prior art compound di-t-butyl diperoxyfumarate, Preparation 6.

TABLE 4

| Safety Characteristics of Peromyfumarates | | |
|---|---|---|
| | Results | |
| Safety Test | Preparation 1 | Preparation 6 |
| Shock Sensitivity, inches | >20 | 3 |
| Trauzl Number, mL | 20 | 72 |
| Rapid Heat | 96° C., Rapid Gassing | 70° C., Very Rapid Decomposition |

EXAMPLE 17

100° C. SPI Exotherm Data for Peroxyfumarate Composition Preparation 1

The unsaturated polyester resin composition used in this example was a mixture of an unsaturated polyester and styrene monomer. The unsaturated polyester was an alkyd resin made by esterifying the following components:

| Component | Quantity (moles) |
|---|---|
| Maleic Anhydride | 1.0 |
| Phthalic Anhydride | 1.0 |
| Propylene Glycol | 2.2 |

To the resulting resin was added 0.013% by weight of hydroquinone inhibitor. The alkyd resin had an Acid No. of 45–50. 7 parts by weight of the above unsaturated polyester alkyd was diluted with 3 parts by weight of monomeric styrene. The resulting unsaturated polyester resin composition had the following properties:

a. Viscosity (Brookfield No. 2 at 20 r.p.m.): 13.0 poise
b. Specific gravity: 1.14

Gelation and cure characteristics of t-butyl perbenzoate (t-BP), a well-known curing catalyst for unsaturated polyester resin compositions, the novel peroxyfumarate composition Preparation 1, of the present invention and pure OO-t-butyl O-ethyl monoperoxyfumarate (t-BEMPF), a prior art monoperoxyfumarate, were determined using the Standard SPI Exotherm Procedure as set forth in SUGGESTED SPI PROCEDURE—Procedure for Running Exotherm Curves Using Thermocouple Needle, 24th Annual Technical Conference (1969), Reinforced Plastics/Composites Division, the Society of the Plastics Industry, Inc., p. 6. Using the procedure at 100° C., t-BEMPF, t-BP and Preparation 1 were evaluated. The results are summarized in Table 5 and show that Preparation 1 is highly active in gelling and curing the unsaturated polyester resin compared to prior art curing agent t-BP.

TABLE 5

SPI Exotherm Data at 100° C.

| Curing Catalyst | Level (%) | Gel Time (min) | Cure Time (min) | Peak Exotherm (°F.) | Barcol Hardness |
|---|---|---|---|---|---|
| t-BEMPF | 1.0 | 5.4 | 7.9 | 392 | 45–50 |
| t-BP | 1.0 | 7.8 | 9.9 | 387 | 45–50 |
| Preparation 1 | 1.0 | 6.0 | 8.6 | 366 | 45–50 |

The present invention may be embodied in other specific forms without departing from the spirit or essential attributes thereof and, accordingly, reference should be made to the appended claims, rather than to the foregoing specification as indicating the scope of the invention.

I claim:

1. A process selected from the group consisting of:
a process for curing an unsaturated polyester resin comprising heating the resin in the presence of an amount of a peroxyester composition as defined herein and at a temperature effective to cure the polyester resin composition;
a process for polymerizing an ethylenically unsaturated monomer comprising heating the monomer in the presence of an amount of a peroxyester composition as defined herein and at a temperature effective to initiate polymerization of the monomer;
a process for preparing a polymeric peroxide comprising one or more ethylenically unsaturated monomers with an amount of peroxyester composition defined herein and at a temperature effective for the peroxyester composition to self-initiate polymerization;
a process for preparing a polymeric peroxide comprising homopolymerizing or copolymerizing a peroxyester composition as defined herein in the presence or absence of one or more ethylenically unsaturated monomers at a temperature and in the presence of at least one free-radical initiator effective to initiate polymerization; and
a process for preparing a polymeric peroxide comprising reacting at least one polymer or copolymer having labile carbon-hydrogen bonds with the peroxyester composition defined herein in the presence of an amount of a polymerization initiator and at a temperature effective to initiate polymerization,

Wherein the peroxyester composition used, in said processes comprises about 0.04 to about 0.70 mole fraction of a first component compound having formula I:

about 0.32 to about 0.50 mole fraction of a second component compound having a formula II:

about 0.04 to about 0.70 mole fraction of a third component compound having a formula III:

the mole fractions being determined by the respective molar quantities of the three components present in the peroxyester composition;
wherein
Q is a divalent radical having a formula IV, V, or VI:

IV

V

VI

R is substituted or unsubstituted alkyl of 1 to 18 carbons optionally containing one or more —O— or —NH— hereto groups, with the proviso that multiple hetero groups must be separated from each other and the radical ends by at least one carbon atom, substituted or unsubstituted cycloalkyl of 5 to 12 carbons, substituted or unsubstituted alkenyl of 3 to 11 carbons, substituted or unsubstituted aryl of 6 to 14 carbons or substituted or unsubstituted aralkyl of 7 to 11 carbons, where the R substituents are one or more of lower alkyl of 1 to 4 carbons, chloro, bromo, cyano, carboxy, alkoxy of 1 to 10 carbons or aryloxy of 6 to 10 carbons;
$R^1$ is substituted or unsubstituted t-alkyl of 4 to 12 carbons, substituted or unsubstituted t-alkynyl of 5 to 9 carbons, substituted or unsubstituted t-cycloalkyl of 6 to 13 carbons or substituted or unsubstituted t-aralkyl of 9 to 13 carbons, where the $R^1$ substituents are independently one or more of lower alkyl of 1 to 4 carbons, chloro, hydroxy or t-alkylperoxy of 4 to 8 carbons; and
from zero to about 250% by weight of a solvent, based upon the total weight of the three components of the peroxyester composition having formulas I, II and III.

2. A process for curing an unsaturated polyester resin as defined in claim 1.

3. A process for polymerizing an ethylenically unsaturated monomer as defined in claim 1.

4. A process for polymerizing an ethylenically unsaturated monomer as defined in claim 1.

5. A process for preparing a polymeric peroxide comprising polymerizing one or more ethylenically unsaturated monomers in the presence of a peroxyester composition at a temperature effective for said peroxyester composition to self-initiate polymerization as defined in claim 1.

6. A process of preparing a polymeric peroxide comprising homopolymerizing or copolymerizing a peroxyester composition in the presence or absence of one or more ethylenically unsaturated monomers and at least one free radical initiator as defined in claim 1.

7. A process for preparing a polymeric peroxide comprising reacting a peroxyester composition with at least one polymer or copolymer having labile carbon-hydrogen bonds as defined in claim 1.

8. The process according to claim 7 wherein the polymerization initiator is the peroxyester composition of claim 1 in an amount sufficient to be a self-initiator.

9. The process according to claim 7 wherein the polymerization initiator is ionizing radiation.

10. The process according to claim 7 wherein the polymerization initiator is one or more free-radical initiator compounds.

* * * * *